(12) United States Patent  
Bihn

(10) Patent No.: US 10,850,023 B2  
(45) Date of Patent: Dec. 1, 2020

(54) DIABETIC MEDICATION DELIVERY PEN PACKET

(71) Applicant: Hunter S. Bihn, Perrysburg, OH (US)

(72) Inventor: Hunter S. Bihn, Perrysburg, OH (US)

( * ) Notice: Subject to any disclaimer, the term of this patent is extended or adjusted under 35 U.S.C. 154(b) by 694 days.

(21) Appl. No.: 15/502,058

(22) PCT Filed: Aug. 5, 2015

(86) PCT No.: PCT/US2015/043834  
§ 371 (c)(1),  
(2) Date: Feb. 6, 2017

(87) PCT Pub. No.: WO2016/022704  
PCT Pub. Date: Feb. 11, 2016

(65) Prior Publication Data  
US 2017/0232184 A1  Aug. 17, 2017

Related U.S. Application Data

(60) Provisional application No. 62/033,579, filed on Aug. 5, 2014.

(51) Int. Cl.  
*A61M 5/00* (2006.01)  
*A61M 5/32* (2006.01)  
(Continued)

(52) U.S. Cl.  
CPC ......... *A61M 5/003* (2013.01); *A61B 5/14532* (2013.01); *A61B 5/151* (2013.01);  
(Continued)

(58) Field of Classification Search  
CPC ..... A61B 5/14532; A61B 5/151; A61B 5/157; A61B 5/4839; A61B 50/362;  
(Continued)

(56) References Cited

U.S. PATENT DOCUMENTS 4,494,652 A * 1/1985 Nelson ................ A61M 5/3205  
206/366  
4,826,073 A * 5/1989 Bruno ................. A61M 5/3205  
206/366  
(Continued)

FOREIGN PATENT DOCUMENTS

JP  2012075628 A * 4/2012

*Primary Examiner* — Chun Hoi Cheung  
*Assistant Examiner* — Brijesh V. Patel  
(74) *Attorney, Agent, or Firm* — MacMillan, Sobanski & Todd, LLC

(57) ABSTRACT

A packet for a medication delivery pen comprises a pen cap integrally connected to one, some, or all of the devices listed: an unused pen needle dispenser, sharps container for used needles, folding glucose monitor, constant glucose monitor, glucose tablets/candy, lancing device, or glucose test strip holder. The integrated pen cap is configured to replace the pen cap normally supplied with the pen and the attachments and devices featured put all items needed by a diabetic in one device. This device also gives the diabetic freedom in choosing which devices they would like to or would like not to carry with them, and in what manner so as to have the highest convenience to the diabetic.

15 Claims, 16 Drawing Sheets

(51) Int. Cl.
  *A61B 5/145* (2006.01)
  *A61B 50/30* (2016.01)
  *A61B 50/36* (2016.01)
  *A61B 5/151* (2006.01)
  *A61B 5/157* (2006.01)
  *A61B 5/00* (2006.01)

(52) U.S. Cl.
  CPC ............ *A61B 5/157* (2013.01); *A61B 5/4839* (2013.01); *A61B 50/3001* (2016.02); *A61B 50/362* (2016.02); *A61M 5/3205* (2013.01); *A61B 2560/04* (2013.01); *A61B 2560/0418* (2013.01); *A61B 2562/0295* (2013.01); *A61M 2005/004* (2013.01)

(58) Field of Classification Search
  CPC ........ A61B 50/3001; A61B 2562/0295; A61B 2560/0418; A61M 5/003; A61M 5/3205; A61M 2005/004
  USPC ................. 206/216, 363–366, 380, 383, 570
  See application file for complete search history.

(56) References Cited

U.S. PATENT DOCUMENTS

| | | | |
|---|---|---|---|
| 5,245,117 A * | 9/1993 | Withers | A61M 5/3205 206/366 |
| 5,279,294 A * | 1/1994 | Anderson | A61B 5/14532 600/322 |
| 5,545,145 A * | 8/1996 | Clinton | A61M 5/002 206/366 |
| 6,250,465 B1 * | 6/2001 | Daniels | B65F 1/10 206/370 |
| 6,439,276 B1 * | 8/2002 | Wood | A61M 5/1782 141/27 |
| 6,923,319 B1 * | 8/2005 | Erickson | A61M 5/008 206/366 |
| 8,915,362 B2 * | 12/2014 | Erickson | A61M 5/3205 206/366 |
| 8,944,245 B2 * | 2/2015 | Erickson | A61M 5/3205 206/345 |
| 2002/0013522 A1 * | 1/2002 | Lav | A61B 5/14532 600/365 |
| 2003/0191415 A1 * | 10/2003 | Moerman | A61B 5/157 600/584 |
| 2005/0143675 A1 * | 6/2005 | Neel | A61B 5/150305 600/583 |
| 2006/0243635 A1 * | 11/2006 | Sullivan | A61B 17/3217 206/571 |
| 2011/0094909 A1 * | 4/2011 | Leabeater | A61M 5/3205 206/365 |
| 2012/0041382 A1 * | 2/2012 | Chapin | A61M 5/002 604/192 |
| 2012/0089051 A1 * | 4/2012 | Draudt | A61B 5/14532 600/583 |

* cited by examiner

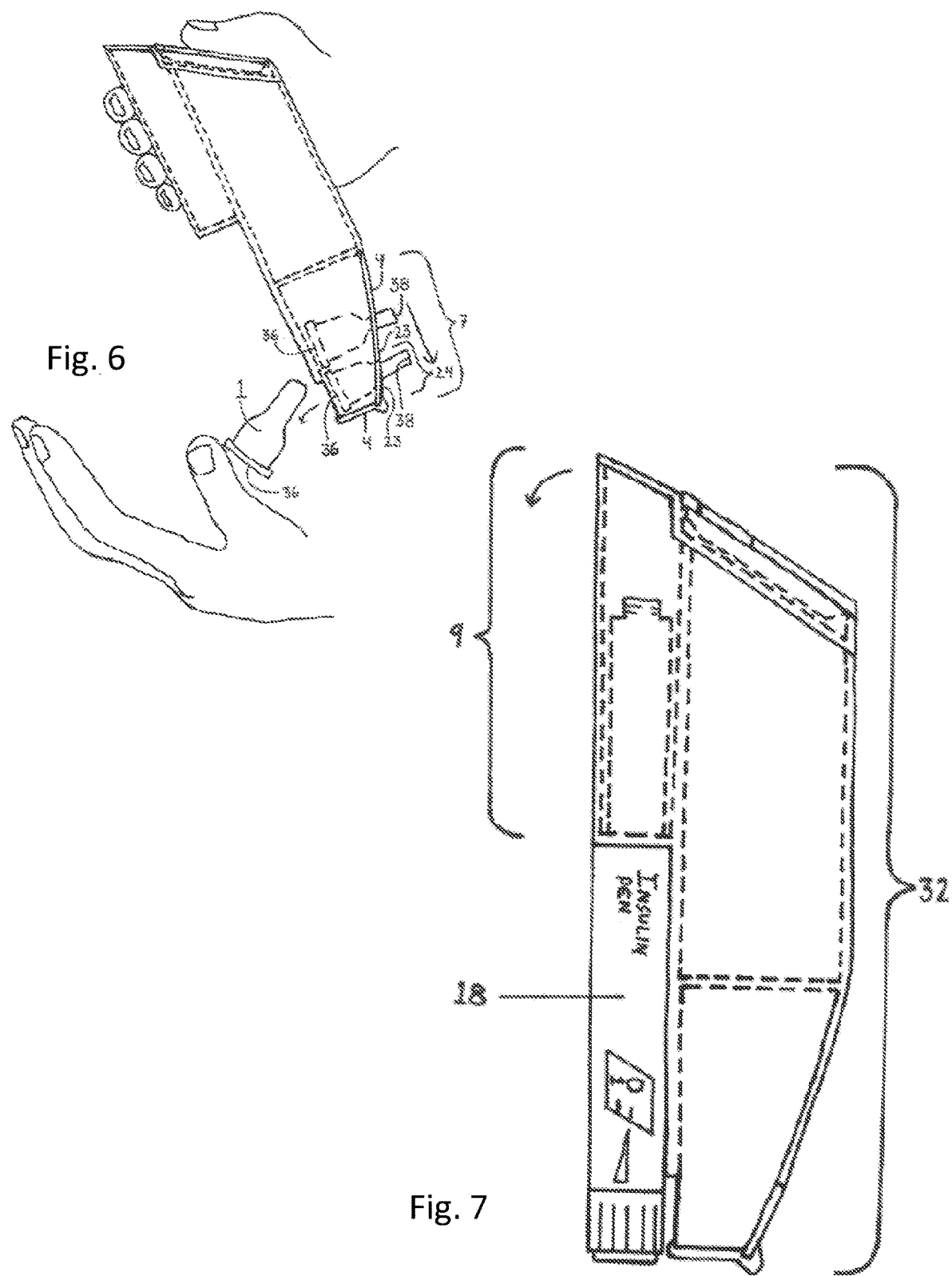

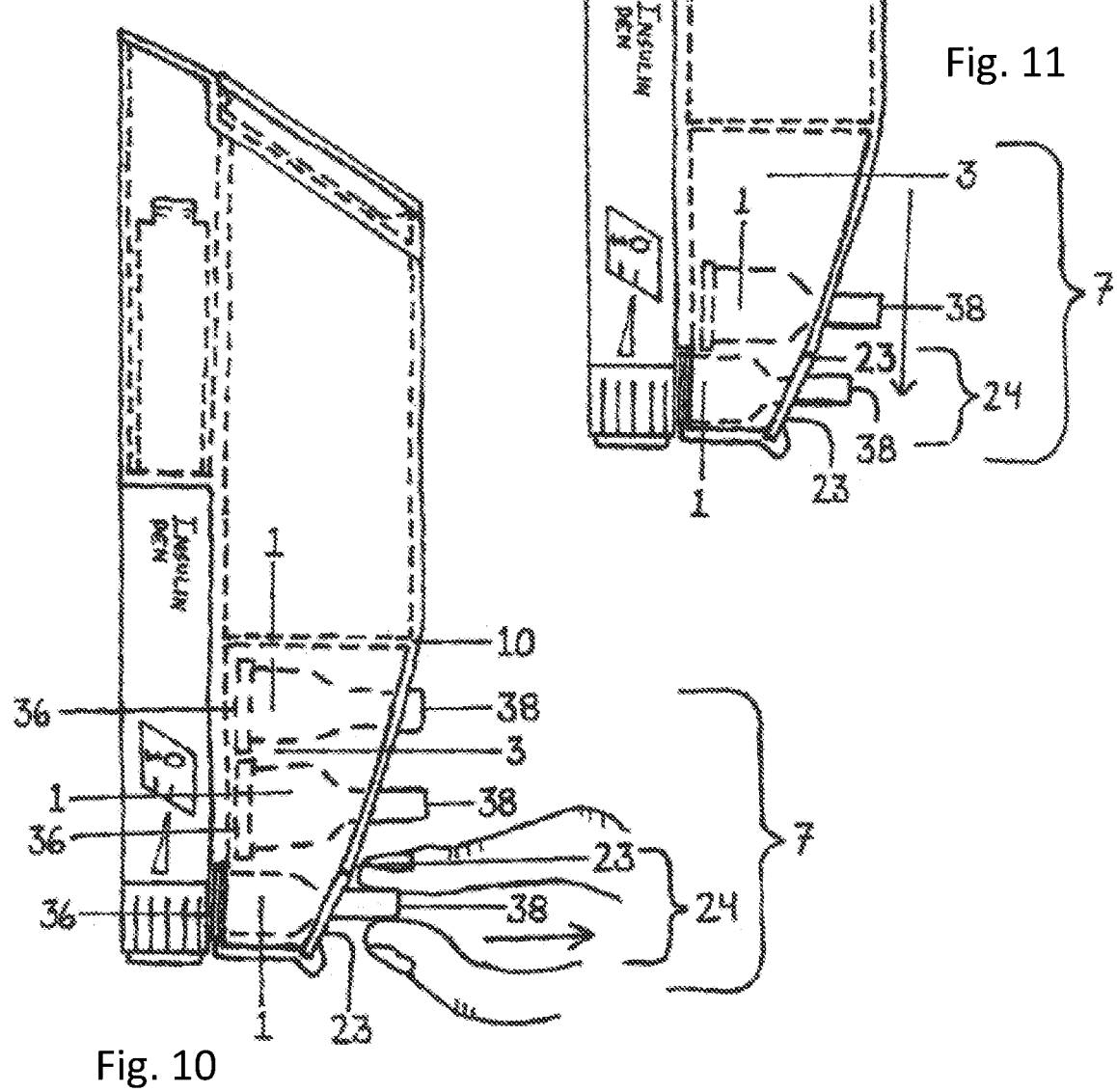

DIABETIC MEDICATION DELIVERY PEN PACKET

CROSS-REFERENCE TO RELATED APPLICATIONS

This application is the National Phase of International Application PCT/US2015/043834 filed Aug. 5, 2015 which designated the U.S. and that International Application was published in English under PCT Article 21(2) on Feb. 11, 2016 as International Publication Number WO2016/022704A1. PCT/US2015/043834 claims priority to U.S. Provisional Application No. 62/033,579, filed Aug. 5, 2014. Thus, the subject nonprovisional application claims priority to U.S. Provisional Application No. 62/033,579, filed Aug. 5, 2014. The disclosures of both applications are incorporated herein by reference.

BACKGROUND OF THE INVENTION

This invention relates to a device for use by diabetics and other medical patients who must use hypodermic needles to inject medication at home or on-the-go with the use of medication delivery pen commonly referred to as an "EpiPen" or an insulin pen. These medication delivery pens contain a large amount of medication with a dial to select a small portion of that medication to be used in a single dosing. To use an insulin pen, a disposable pen needle is screwed in, used, then unscrewed and removed from the medication delivery pen. The disposable pen needle has a thin removable foil backing in order to keep the needle sterile until use. This backing is removed leaving the end of the cap-covered pen needle that is to be screwed into the medication delivery pen exposed. This end is screwed into the end of the medication delivery pen (or insulin pen) and the cap covering the needle inside is then removed to leave a needle exposed and attached to the medical delivery pen. The patient then dials the precise amount of insulin or other medication needed with a dial on the medical delivery pen and injects the medication. The needle is then recapped and unscrewed from the medication delivery pen, leaving the patient with both the foil covering for the back of the needle and the contaminated pen needle itself. The patient takes this medication when they are hyperglycemic (high blood glucose).

As well, to know whether or not to give an insulin injection, do nothing, or consume glucose/carbohydrates, diabetics must monitor their blood glucose using a blood glucose monitor. This monitor tells them if they are hyperglycemic (high blood sugar requiring dieting, exercise or the injection of insulin) or hypoglycemic (low blood sugar requiring the diabetic to ingest glucose/carbohydrates). There are currently two primary forms of blood glucose monitor systems. One form, referred to as the "traditional" form has three common necessary devices associated with it. The traditional style glucose monitor system requires disposable blood testing strips in a holding container, a finger lancing device to draw blood, and a monitor to put the testing strip into and read the blood glucose. The second method is a constant glucose monitor that checks the blood glucose at regular intervals using a patch that has a probe. The probe sits subcutaneously and reads blood glucose, sending the results to a blood glucose monitor. The final necessary component that a diabetic must carry besides a glucose monitor and insulin is then some form of carbohydrate or glucose with them in order to raise their blood sugar if they are hypoglycemic (low blood glucose). This comes in the form of candy or blood glucose tablets most often.

With both the glucose monitor and the insulin pen there comes considerable medical waste in the form of contaminated insulin pen needles, lancets, and test strips. These all constitute medical waste and pose a considerable risk to public safety due to risk of exposure to blood borne pathogens, especially considering the prevalence of diabetes and the millions of people using these medical devices. The problem becomes that while hospitals necessitate the proper disposal of any contaminated sharps, in personal use these pen needle caps and other contaminated medical wastes are often times left around in houses, cars, pockets, and bags since there lacks a way to easily dispose of these products on-the-go. In addition to this, when pen needles are not disposed of immediately following use patients will often times reuse the needles since they are readily available. This poses a risk to the patient and may cause accidental exposure to blood borne pathogens in the environment around the patient.

It is also important to note the logistics of a diabetic or other medication delivery pen using patient's devices that they carry with them. Medication delivery pens, due to their smooth, straight, and rounded nature often times fall out of pockets, bags and purses. The same goes for the unused pen needles that are freely scattered throughout pockets and purses making them also easily fall out. If pen needles do stay in a bag or purse, they may also be hard to find since they are small and can easily hide among the numerous other products in the purse or bag.

Diabetics and other patients using these pens are also burdened due to the need to carry a number of medical devices with them daily. As individuals, even non-diabetics often carry a wallet or purse, keys, and a cell phone in daily life. Diabetics must also then carry some form of glucose/carbohydrate, a glucose monitor, their insulin pen, and insulin pen needles. This is seven items needed daily, and this is without a way to properly dispose of the medical waste. Currently, many diabetics leave necessary devices at home because of the inconvenience of carrying all the devices necessary for proper blood glucose management. The addition of any extra medical device would be a further burden and likely cause them not to use such a device. The pairing of these devices together into one device that can be easily carried then lessons the chances that one device will be left, forgotten, lost, or otherwise not available for use when a diabetic needs it. As well, it is important to offer the diabetics options in the manner that they may carry the devices, since everyone has preferences and individual lifestyles that they mold to fit around the way they manage their disease.

SUMMARY OF THE INVENTION

The base device of this invention looks to solve the problems relating to injecting with the insulin pen and the medical waste created by diabetes. In one embodiment, it is a disposable device that allows the patient to both store pen needles and properly dispose of all medical waste associated with diabetes or other diseases requiring a medication delivery pen. The base device of the invention would do so without the burden of carrying any extra medical device. It would do so by attaching directly to the medication delivery pen itself in replacement of the medication delivery pen's cap, with the sharps container and unused pen needle dispenser hanging on one side of the pen. This would be done in such a way as to add little to its noticeable carrying size of the medication delivery pen. This portion of the invention would be as long as the pen itself, add just slightly more to the width of the pen than a medication deliver pen needle laid horizontally, and would be just slightly larger in depth than the diameter of the original pen and needles. This would be the base of the entire invention with a glucose monitor and/or glucose tablets attaching to this device at the discretion of the diabetic. It would allow diabetics a disposable device that carries both the unused needles necessary to make an injection and a disposal area for contaminated pen needles, lancets, test strips, and any small materials associated with diabetes and diabetic devices. There is no prior devices or ideas filed that attach a sharps container, disposal container, or pen needle storage device to the pen in replacement of its pen cap. As well, there is no system that attaches to the pen that preferentially stores the needles horizontally.

This invention then also features removable additions to allow for both a folding blood glucose monitor or constant glucose monitor and glucose tablets/candy so that the diabetic has the option of carrying all necessary devices and materials related to diabetes in one pocket sized device. These additions would attach to the unused needle holder and disposal container by clipping onto the replacement pen cap opposite the disposal container/unused needle dispenser or separately via their own pen cap replacement. The optional attachment options featured in the invention are a folding glucose monitor, constant glucose monitor, or glucose tablets/candy. Each of the attachments can be attached individually to the unused needle holder/disposal container.

The glucose tablets/candy will also features a second identical clip as the one it attaches to on the outside of the glucose tablets/candy that allows for either the folding glucose monitor or constant glucose monitor to be attached to the outside. When all three devices are together the glucose tablets/candy attachment then sits in between the disposal container/unused needle holder and the glucose monitor of choice. As well, when all three devices are put together (the disposal container/unused needle holder, constant or foldable glucose monitor, and the glucose tablets/candy) then all devices needed to check blood sugar and properly take care of hyperglycemia or hypoglycemia are in one device. The glucose tablets/candy can also be attached to just the glucose monitor. There is currently no device that combines any and certainly not all of these devices in such a way.

The disposal container and pen needle dispenser cap features a double-dispensing method of carrying unused needles that both allows for two differing methods of dispensing needles. This allows for an affordable method of production since the hinged door used allows the invention to be produced in only two mold cavities. Making the device as low cost as possible to manufacture is necessary for the device to be disposable. This is the minimum necessary cavities needed to manufacture this device since the cap of the invention can be produced with a different plastic than the body to allow the teeth to flex and allow used needles to fall through. This makes the invention inexpensive to produce.

The first method of dispensing involves the medication delivery pen being removed as it would be to take a shot. In order to load the needles the pen is flipped upside down as it is removed, exposing a hole in the very posterior of the invention on the side that runs along the medication delivery pen. The needles are fed into this hole, pointed end first so they poke through the opening opposite of the hole, with the side with the plastic covering that keeps the needle sterile entering last. The needles are stacked inside similar to how shotgun shells are loaded, with the pointed end facing away from where the medication delivery pen would be and the needles lying horizontally. No prior device that attaches to the insulin pen to hold the pen needles stacks them horizontally. In order for this to be accomplished the end opposite of the opening in the posterior also has a triangular opening that runs along the hinged door that is smaller than the foil end of the unused pen needle so the pointed end of the needles may stick out, but not fall out since that opening is not as large as the diameter of the pen needle's largest side. The medication delivery pen is then replaced and this keeps the needles from falling out before use.

When the pen is to be used the user removes the pen and angles the invention so an unused pen needle falls out the hole that is now exposed since the medication delivery pen is no longer present to stop it. A new needle then falls into the place of the needle that has just been dispensed due to gravity and is ready for use. The medication delivery pen and pen needle are then used. The pen is replaced and the hole is covered. The user then dispenses the pen needle and coverings into the sharps container into the top of the device under the angled lid and disposes of them.

In the second method of dispensing unused needles involves the medication delivery pen staying in place. The user flips the device upside down, uses their thumb to open the living hinge door at the bottom of the device that is adjacent and opposite to the opening described in the previous dispensing method. Once the door is opened, the needles are placed inside again with the pointed end of the needles facing away from the medication delivery pen, horizontally. The door is then closed allowing the pointed ends to again stick through the opening on the door itself.

This opening on the door starts smallest at the top of the unused needle containment area and generally gets wider towards the bottom, with plastic teeth along the opening. This is for two reasons. The first is that the door angles back towards the pen needle, requiring more of the triangular shaped pen needle to stick out of the door. The second and main purpose of this is to allow for the needle at the very bottom, where the opening is only slightly smaller than the needle due to the plastic teeth in the opening, to be pulled through these teeth as they flex slightly.

This method is meant to have unused needle dispensing be similar to grabbing a number to wait in line at a restaurant or butcher shop, making it natural and easy to use. The needle is pulled through the teeth and in its place, gravity again causes a new needle to fall down and replace it. It is important to note that any loading or dispensing method may be used at any time to the user's preference. The order listed in here is to make the device's functions easy to understand and visualize. Also, the depth of the device is only slightly larger than the diameter of the pen needles, forcing the needles to lie horizontally in the unused needle containment area and horizontally or vertically in the sharps containment area. It is preferable that they not lie cross with the length of the device.

Once the pen needle, lancets, tests strips, or other contaminated medical products have been used the user then will open the lid to the sharps container located at the top of the invention. This sharps container features an angled lid that serves a few purposes. The first purpose is the angle to the lid opens and fits naturally under the user's thumb as the needle is inserted. This is meant to be a good use of ergonomics and is important to the acceptance of the device. The needle is to be placed under the opened lid and on top of the plastic teeth with the pointed end closest to the hinge so it is on a downward angle. The second purpose of the lid is to increase the length of the hole through which the needle is pushed through since the width of the containment area (width being from the side that runs along the length of the medication delivery pen, to the side opposite that has the triangular opening in at the lower end) is only very slightly longer than the length of pen needle. The angle uses the concept of Pythagorean's Theorem (basic geometry) to increase the length of opening. The user then also puts any extra smaller pieces to the pen needle (such as the foil) or any contaminated waste medical products that can fit underneath the lid with the pen needle.

The user then presses down on the top of the lid in a natural motion to close the lid, with the lid protecting his or her thumb. The lid may feature a groove for the user's thumb so their thumb does not to slip out and this groove assists in pushing the pen needle, lancets, or test strips through the plastic teeth into the containment area. Once this motion is executed, the lid seals tightly and securely until it is opened again and all contaminated medical products are kept permanently in the containment area by the flexible plastic teeth. The angle to the lid then serves to assist in the needle preferentially falling horizontally into the containment area as the smaller end of the needle (the non-foil side) hits first and breaks the fall of the needle. The inventor in testing different methods found that this was the best way to get the needles to fall horizontally, since when dropped perfectly horizontally the larger back end of the pen needles had a tendency to bounce more causing them to land upright.

While horizontal containment is preferable, it may be difficult to ensure this configuration. The containment area accounts for this due to the diameter of pen needles being a 1:2 ratio to their length. The containment area is only slightly larger in depth than the diameter of the needles and only slightly longer in width than the pen needle's length, meaning they will fall either upright or horizontally. If they fail to fall horizontally, the 1:2 ratio of diameter to length means that two needles stacked vertically occupy the same space in the containment area as two needles that fell horizontally, ensuring the most efficient use of space in the containment area.

The first attachment to the disposal container/unused needle holder is then a folding glucose monitor that both holds test strips and has a lancing device at the bottom. The monitor can be attached or detached from the device via the top half of the folding device (the monitor itself). The second half of the device features a glucose testing strip holder at the top of the lower half and a lancing device at the bottom of the lower half. The device is designed to be detached and be either left in a straight line similar to that of the insulin pen or fold in half. Since the depth of the glucose monitor is the same throughout the device (see FIG. 1C for a reference indication of depth), when folded it is then a perfectly flat and compact all-in-one glucose monitor. If folded, it can easily attach as a key chain or slide into pockets that are not as deep. If kept straight it more easily slides into longer pockets or bags and it resembles the insulin pen itself. The design both minimizes the space needed to carry all three parts necessary to the glucose monitor and features two different ways to carry the device to maximize convenience to the user.

This detachment of this portion of the invention allows the user to have the option of having one larger device or separate into two smaller devices (glucose monitor/test strips/lancing device and the needle holder/disposal): one to be carried in each pocket or as the patient wishes. If the user has an issue with losing devices, has a large pocket or bag to carry the device, or otherwise wants to easily keep track of all devices (the insulin pen, needles, disposal, and glucose tablets) they can choose to attach them all together. If they wish to separate the devices to fit one in each pocket, they have that option as well. This gives the user the most flexibility to fit this device into their daily life while pairing together devices that go together.

The folding glucose monitor takes three separate devices and pairs them together into one device. Before, these three devices were often times kept in a purse-like bag that held the monitor, lancing device, and test strips: each one a separate piece. With this design, they are all in one device that uses design to make the most efficient use of space.

As well, the pen needles (new and used) and the insulin pen used to be separated and scattered. With the base device to this invention, they are kept with the insulin pen itself. This way the insulin pen has everything needed to make an injection and dispose of used pen needles. Since this portion of the device (the sharps container and unused needle holder) is new, novel and not currently carried with diabetics, it is important to offer the other pieces to which the diabetic may already have strong preferences as attachments. This is because diabetics are often times loyal to the brands they have been using, and are not likely to give up a glucose monitor they have been using for years. This again leaves options open for individual preference.

The design of the glucose monitor at the top of the device, the testing strip holder in the middle, and the lancet at the bottom is the ideal design for both the device folded and unfolded. When used, the test strip to the glucose monitor and the lancing device for one's finger face outward giving easy access. When the attachment is straight, this means that the user lances their finger at the bottom of the device and easily moves it to the top of the device to the inserted test strip. As well when the device is folded, the user needs to just move their finger slightly since the lancing opening and the test strip are right next to one another. Also when folded, the glucose testing strip holder is at the top of the device for the user to most easily remove the blood glucose test strips. The combination of all three devices into one attachment, the layout of the devices in the attachment, and the folding action of the entire device are all unique qualities not seen in any prior devices.

The second attachment available to connect to the disposal container/unused needle holder is a second type of glucose monitor called a constant glucose monitor. A constant glucose monitor is the future of diabetic sugar monitoring since it tracks sugars at regular intervals giving the most information as to the rising or falling of sugar levels throughout the day. The constant glucose monitor would be single device that sends and receives signals to a probe in the form of a patch on the diabetic. It would attach at the same attachment point as the folding glucose monitor and would be a single body piece to receive signals from the probe, process them, and send them to the diabetic. The advantage over other constant glucose monitors is that it attaches to the insulin pen via the cap and the base invention. The fact that this glucose monitor attaches to the base device (disposal container and unused needle holder that attaches in replacement of the medication delivery pen's cap) means that it also attaches to the insulin pen via a replacement cap by proxy.

The final attachment is glucose tablets or candy. The glucose tablets serve to raise a diabetic's blood glucose if they are suffering from hypoglycemia (low blood sugar). This candy attaches at the same attachment point as the glucose monitors and features an identical attachment point on the outside of the glucose tablets/candy so that the glucose monitor of choice by the diabetic can be attached as well, putting all necessary items to manage blood glucose in one device. As well, the glucose tablets/candy can be attached to just the glucose monitor of choice if the user wishes.

Putting the glucose tablets in the center of all three devices (glucose monitor, glucose tablets, and the disposal container/unused needle holder) is important because it allows the diabetic to access the two things they use most, the insulin needles/disposal and blood glucose testing. As well, it allows the diabetic to remove or attach the devices as they choose with the most freedom. It also allows the diabetic to always have glucose tablets with them no matter what other device they are carrying since hypoglycemia (low blood glucose) is the most dangerous immediate threat to a diabetic's life. An important note to be made is the fact that the glucose tablets/candy attaches to the base device (disposal container and unused needle holder that attaches in replacement of the medication delivery pen's cap) this means that it also attaches to the insulin pen via a replacement cap by proxy.

Various aspects of this invention will become apparent to those skilled in the art from the following detailed description of the preferred embodiment, when read in light of the accompanying drawings.

BRIEF DESCRIPTION OF THE DRAWINGS

FIG. 6 is a side view of the base device showing an unused pen needle being dispensed without the medication delivery pen and the remaining needles falling into place.

FIG. 7 is a side view of the empty base device shown with the medication delivery pen inserted and the base device being rotated.

FIG. 10 is a side view of the base device with the medication delivery pen inserted showing the user removing an unused insulin pen needle through the teethed opening at the bottom of the dispensing area.

FIG. 11 is a side view of the base device with the medication delivery pen inserted showing the remaining pen needles falling into place after one has been removed.

DETAILED DESCRIPTION OF THE PREFERRED EMBODIMENTS

Figure 1B:
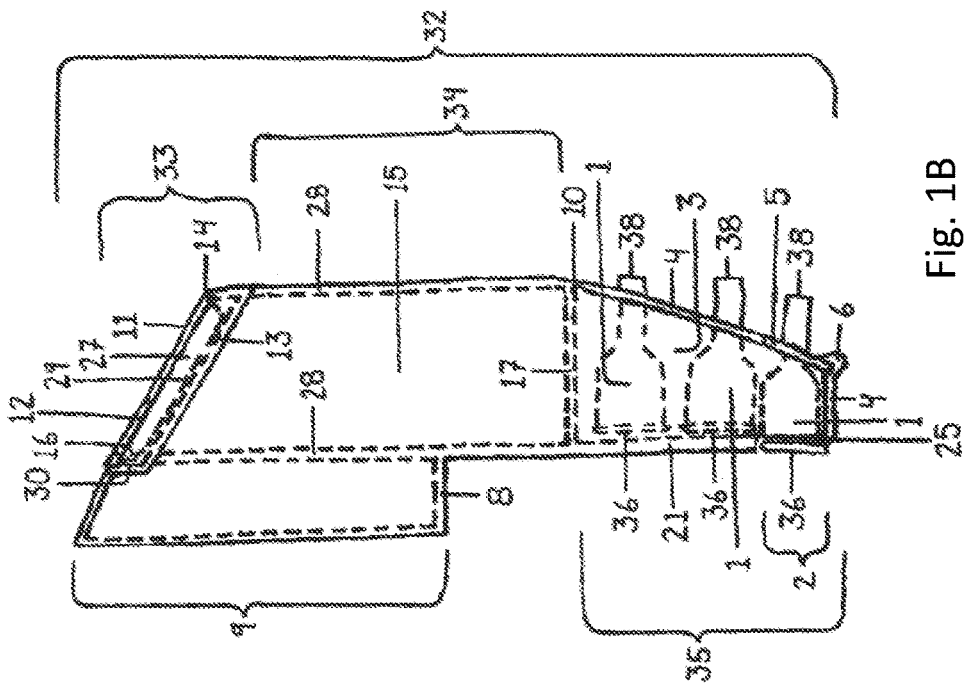
FIG. 1B is a side angle view of the base device with the lid and three unused needles.

FIGS. 1A through 1E show the various parts of the invention. A replacement pen cap disposal container and unused pen needle storage 32 comprises a replacement medication delivery pen cap section 9 that is attached to a sharps containment section 34 (with an angled lid assembly 33 and sharps disposal area 15), and an unused needle containment section 35 (with a hinged door 4 and unused needle storage area 3). Unused pen needles 1 shown with a foil covering on the larger posterior end 36 are held within the unused needle containment area 35 with the foil side 36 of unused pen needles 1 flush against the wall 21 that runs along the medication delivery pen 18, with the bottom needle's foil side 36 flush against the medication delivery pen itself 18 due to the opening 2. The unused needle containment section 35 is made of a solid piece of plastic above 17 and to the sides parallel 22 and a wall behind 21 the foil end of unused pen needles 36, with the curved hinged opening door 4 that has a triangular opening in the center 7 containing teeth 23 and a bottom forming the final two walls (front and back).

Figure 1A:
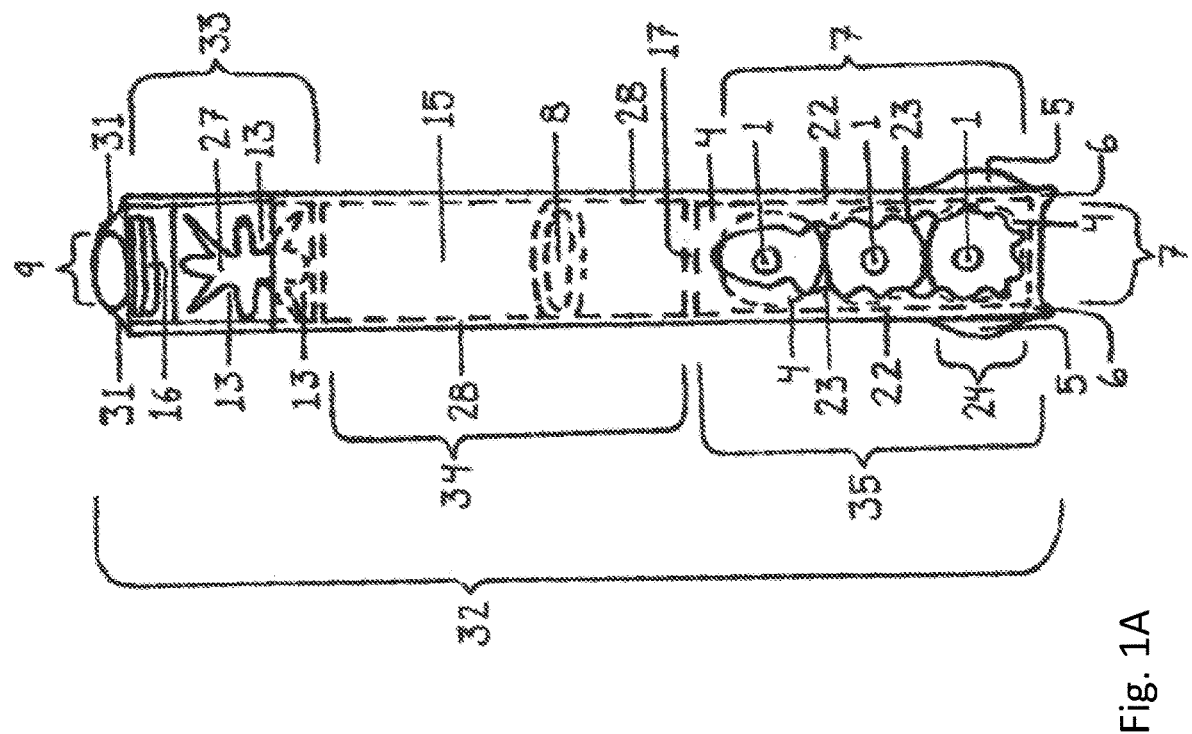
FIG. 1A is a front view of the base device shown with three unused needles and without a lid.
Figure 1C:
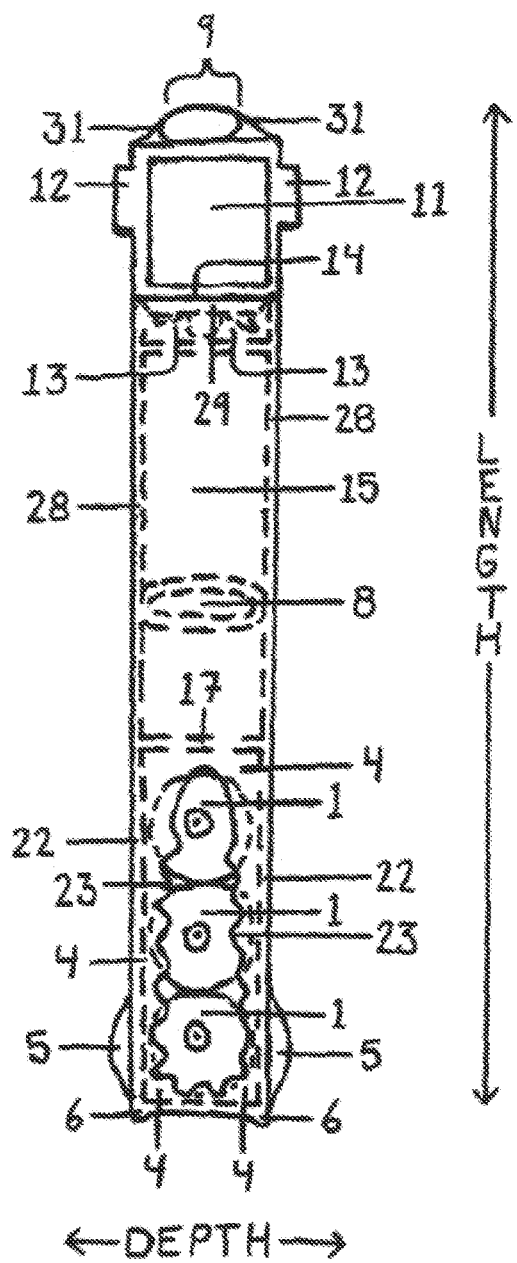
FIG. 1C is a front view of the base device shown with three unused needles and the lid.
Figure 1D:
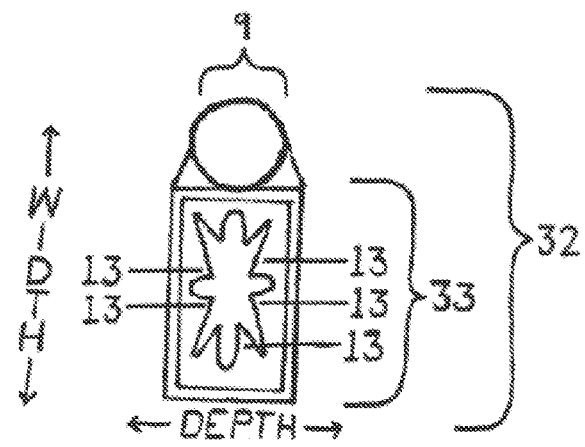
FIG. 1D is a top view of the base device shown without a lid.
Figure 1E:
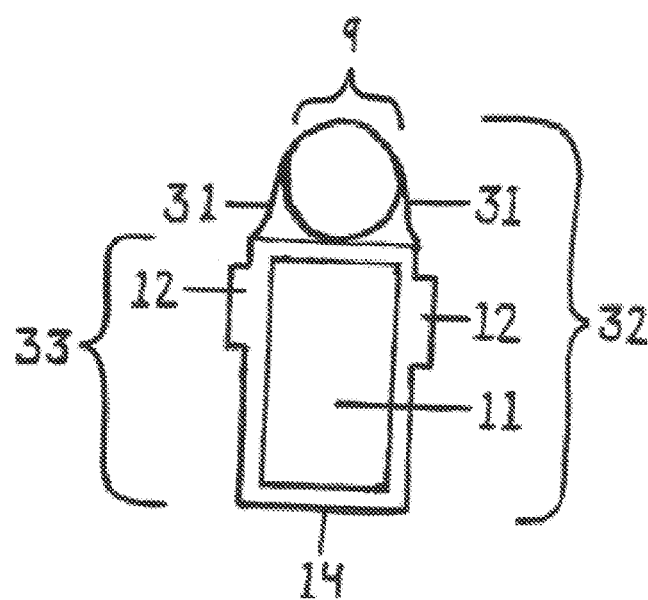
FIG. 1E is a top view of the base device shown with the lid.
Figures 8, 9:
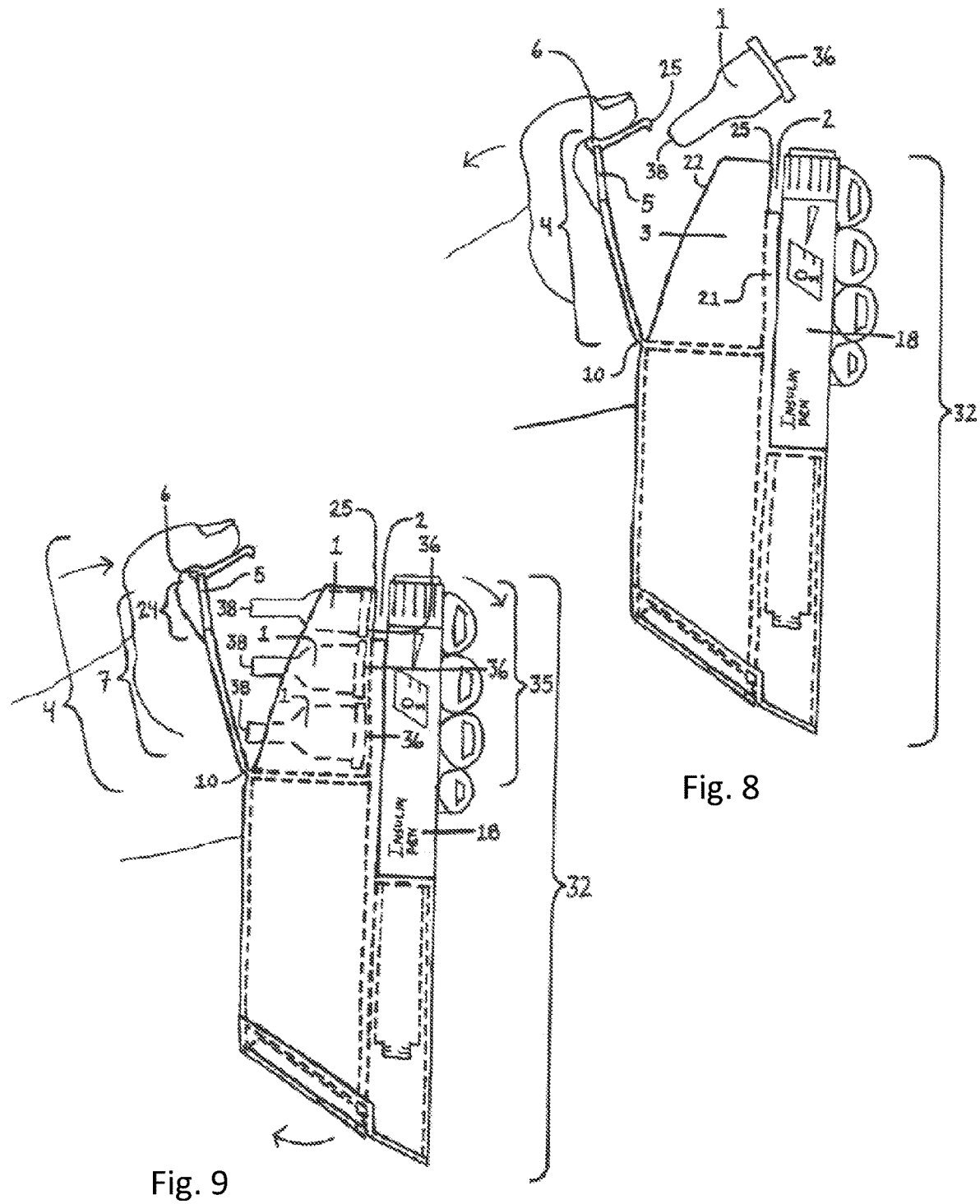
FIG. 8 is a side view of the base device showing the base device inverted with the medication delivery pen inserted and a thumb opening the bottom hinged door to allow unused needles to be placed inside.
FIG. 9 is a side view of the base device with the medication delivery pen inserted showing the thumb closing the hinged door to keep the unused pen needles contained in the dispensing area.

The unused needle storage area 3 is shown in FIGS. 1A through 1C as being only slightly larger in depth than the foil side diameters 36 of the unused insulin pen needles 1. The hinged door 4 has a living hinge 10 at the top of the unused needle storage area 3, with an opening 7 that is a rounded triangular shape. The unused pen needles' 1 non-foil 38 end that comes to a point sticks through this opening 7 with the foil side 36 flush against either the wall 21 running along the medication delivery pen 18 or flush against the medication delivery pen 18 itself at the opening 2. The largest part of the triangle having a circular opening 24 is the same size as the foil side 36 diameters of the unused pen needles 1 and circular in shape, with stiff flexible teeth 23 to hold the pen needle 1 inside until the user wishes to remove a pen needle as shown in FIG. 10. The door has tabs 5 in order to assist in pulling the door free from the latch 25, as shown in FIG. 8. There is also two tabs 6 on the bottom of the hinged door 4 that can also be used for leverage to open the door, or as a stand to hold the device and pen upright when the pen is in place, forming a tripod with the bottom of the medication delivery pen 26 (see FIG. 12).

Figure 5:
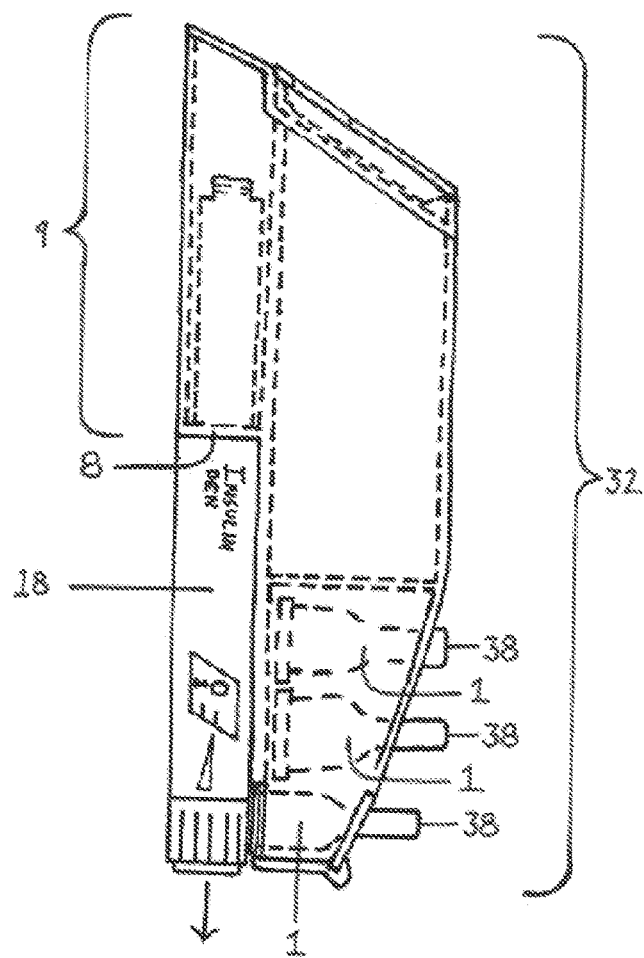
FIG. 5 is a side view of the base device with the three unused pen needles and the medication delivery pen shown being removed.

There is an opening 2 on the medication delivery pen 18 side of the unused pen needle storage section 35 where wall 21 ends, shown to the bottom left in FIG. 1 b. This opening is a square with sides just slightly larger than an unused pen needle's foil side 36 diameter, allowing a needle to be dispersed when the medication delivery pen 18 is removed, as shown in FIGS. 5 and 6. The medication delivery pen 18 slides into the pen cap section 9 that the invention is attached to, and clips-in at the opening 8. This pen cap is much like the medication delivery pen's own cap, being circular in nature but attaches to the slightly wider sharps containment section 34 and unused pen needle storage section 35 as the sides flair out 31.

Figures 12, 13:
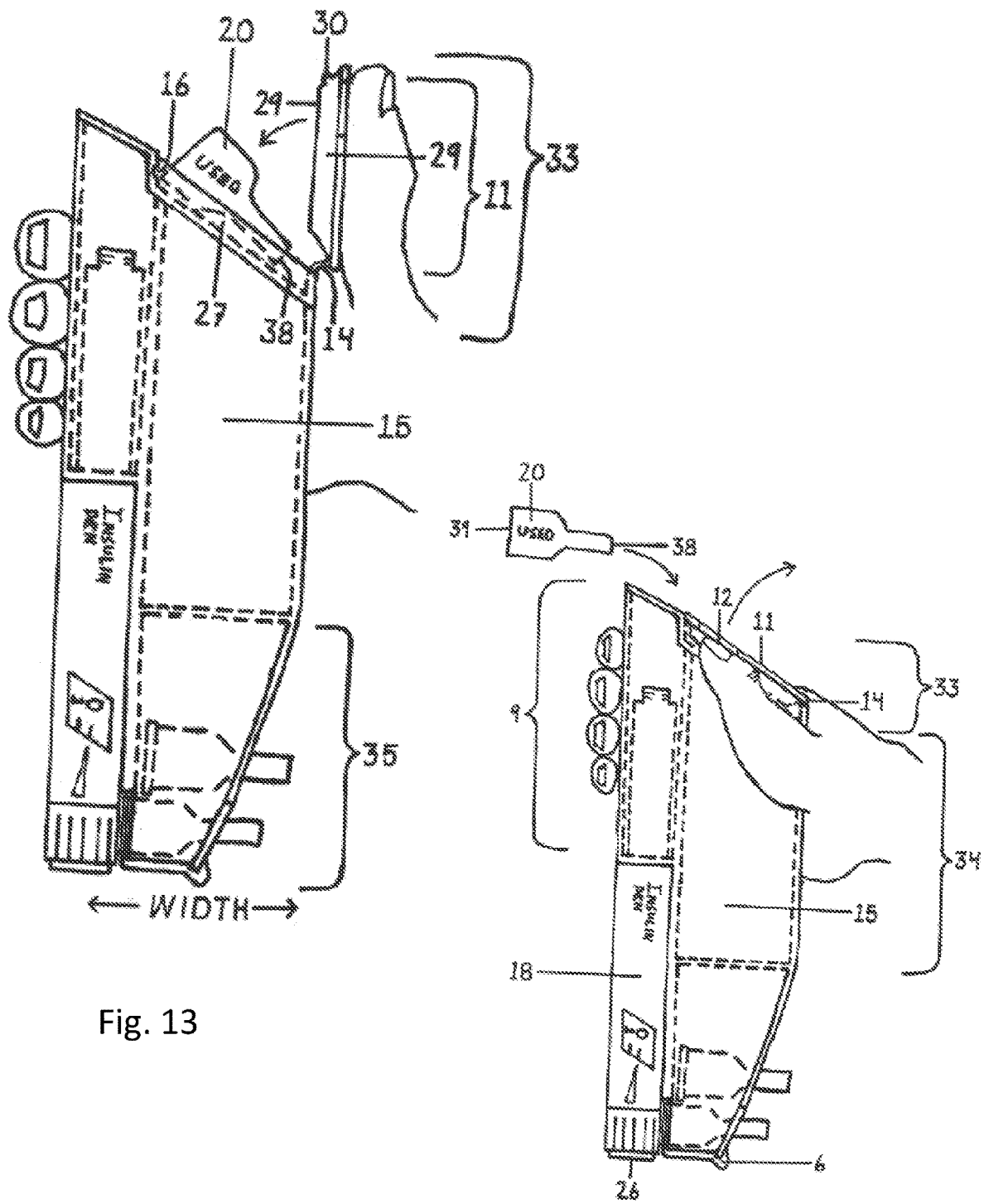
FIG. 12 is a side view of the base device with the medication delivery pen inserted showing a thumb opening the lid to the sharps containment area and a used need being placed in the pre-containment area.
FIG. 13 is a side view of the base device with the medication delivery pen inserted showing the thumb pressing the used needle through the flexible plastic teeth and into the sharps containment area.
Figure 14:
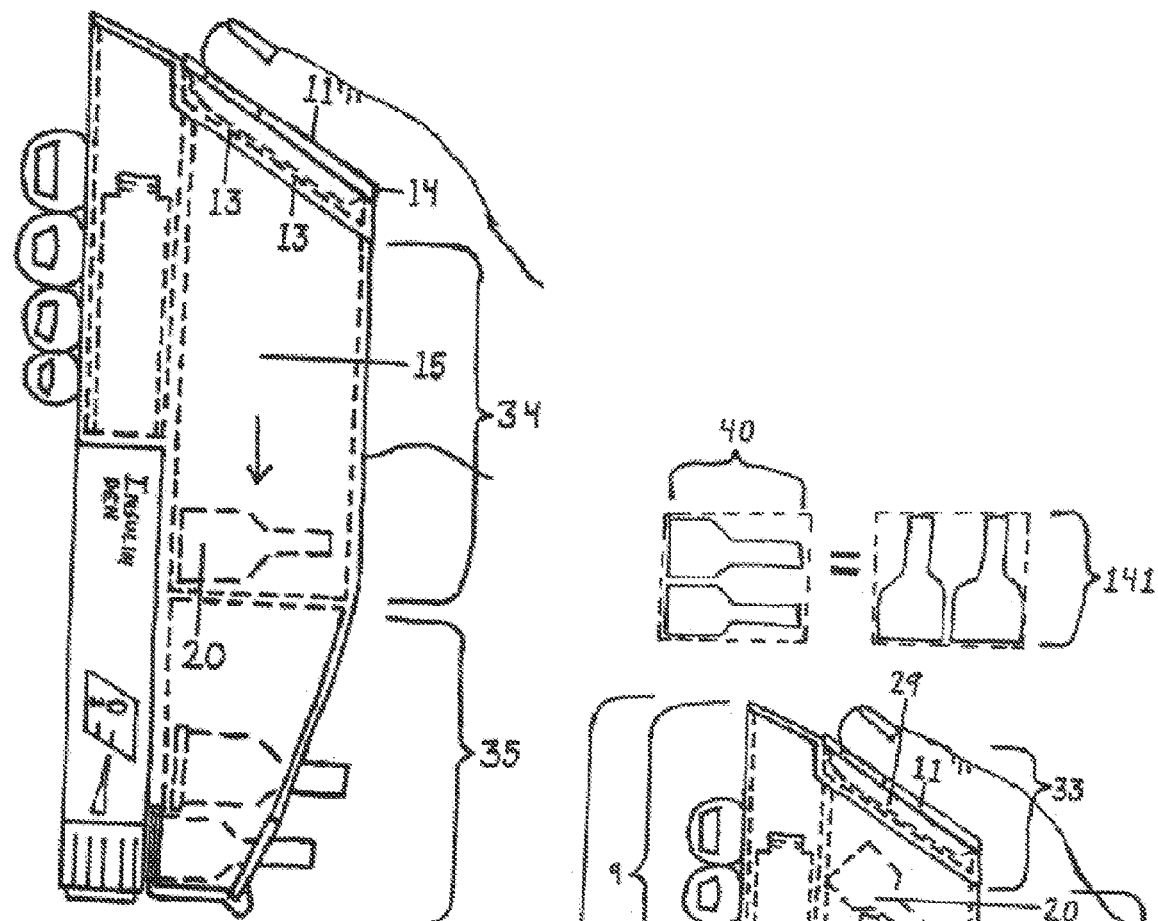
FIG. 14 is a side view of the base device with the medication delivery pen inserted showing the thumb completing the containment action with the lid closed and the pen needle falling horizontally inside.

As shown in FIGS. 12 through 14, the disposal method into the sharps containment section 34 involves a thumb opening the lid using the tabs 12, placing a needle in the pre-containment area 27 on top of the plastic flexible teeth 13, and using the hinged lid 11 to press the used pen needle 20 into the sharps disposal area 15. The living hinge 14 to the lid is located at the bottom of the lid and attached to the lower portion of the sharps containment section 34. The sharps disposal area 15 has four walls 28 and a bottom 17. The four walls 28 and bottom 17 are watertight. The sharps container section comprises the sharps disposal area 15, and the lid assembly 33. The lid assembly 33 comprises the flexible plastic teeth 13, the living hinge 14, the lid itself 11, and the very top part of the pen cap section 9. The lid also features a groove 29 for the user's thumb 29 (see FIG. 13) that prevents the user's thumb from slipping off and helps more completely push medical waste out of the pre-containment area 27, through the flexible plastic teeth 13, and into the sharps disposal area 15. The lid 11 snaps into place due to a groove in the pre-containment area 27 accompanied with a bump 30 on the lid 11. This lid assembly 33 is produced in one mold cavity in production so that the flexible plastic teeth 13 are made from a softer plastic then the rest of the device, which is to be made in a second cavity of the mold from harder plastic for the safety of the user.

Figure 2:
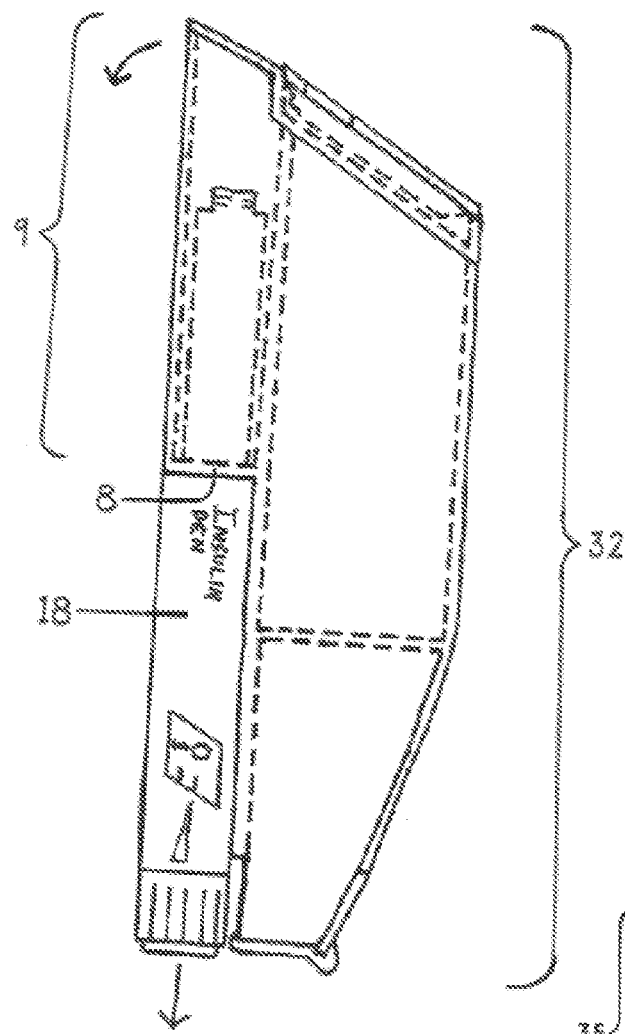
FIG. 2 is a side view of the empty base device with a medication delivery pen inserted with the base device being rotated and the medication delivery pen being removed.
Figure 3:
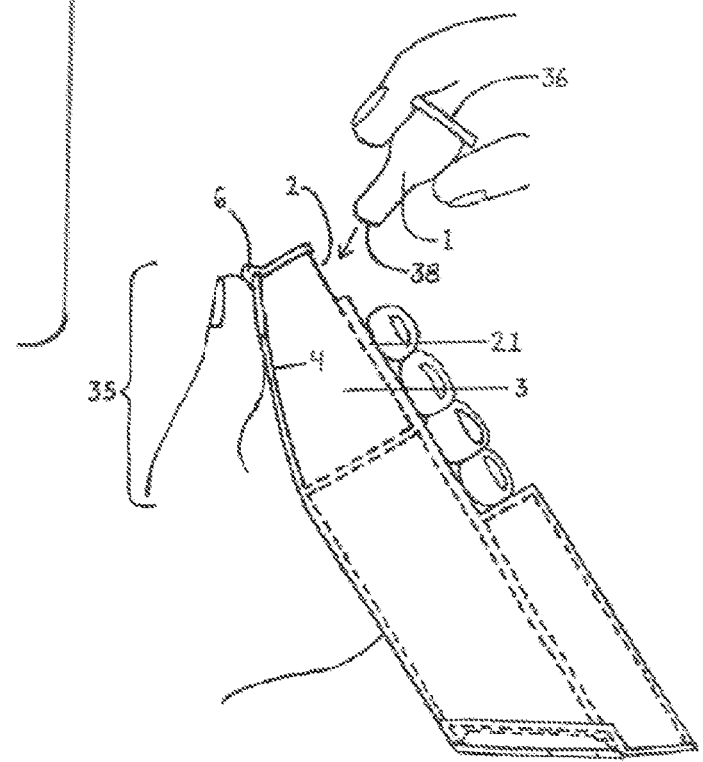
FIG. 3 is a side view of the empty base device shown with an unused pen needle being loaded without the medication delivery pen inserted.
Figure 4:
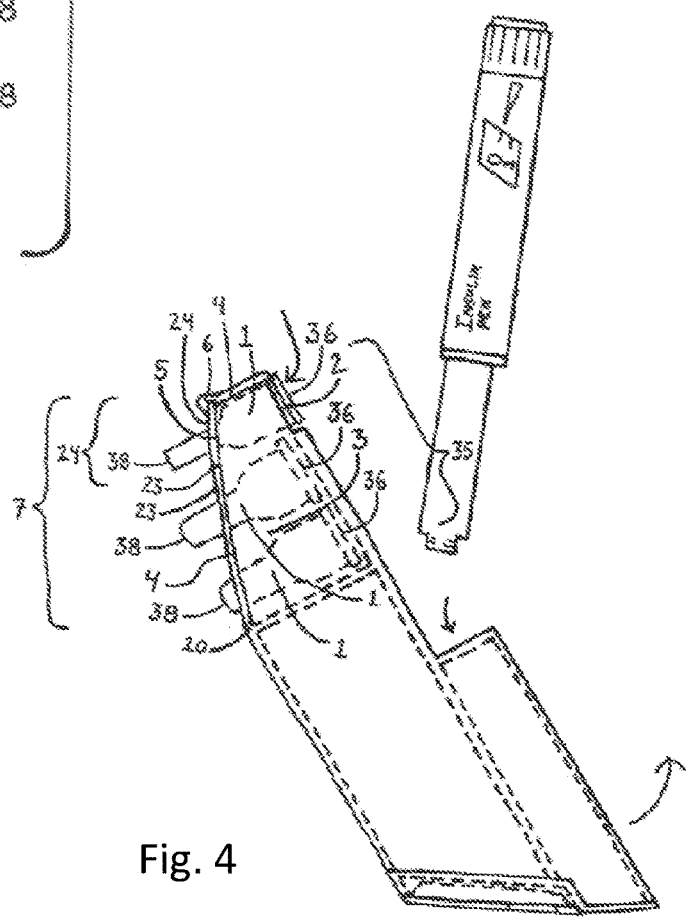
FIG. 4 is a side view of the base device with three unused pen needles loaded and the medication delivery pen being reinserted into its cap.

The first method for dispensing the unused pen needles is shown in FIG. 2 through 6. FIG. 2 shows the medication delivery pen 18 labeled "insulin pen" being removed from the replacement pen cap 9, and being pulled out the opening 8 as the device is rotated so it is inverted. FIG. 3 then shows the unused insulin pen needle 1 being inserted into the unused pen needle storage section 35 of the inverted device through the opening 2 in the lower back portion of the device. The needles fall down to the bottom of the unused pen needle storage section 35 due to gravity, as their backs fall against the rear wall 21. The thumb holds the device steady, resting on the bottom tabs 6. FIG. 4 shows the unused pen needles 1 completely filling the unused pen needle storage area 3, with the smaller non-foil end 38 sticking out through the opening 7 in the hinged door 4. The medication delivery pen system 18 is then shown being replaced into the opening 8 of the device's replacement cap section 9. The entire device is then rotated back upright as the medication delivery pen 18 blocks the unused needle from falling out through the opening in the back 2, while the teeth 23 in the opening 7 in the hinged door 4 keep the needle from falling out the opposite opening 24. FIG. 5 shows the medication delivery pen 18 being removed again from the pen cap 9. FIG. 6 shows that the invention is then rotated so that an unused pen needle 1 falls out the opening 2 now exposed by the missing medication delivery pen 18, and into the user's hand. The remaining unused needles 1 then fall into space left by the dispensed needle, sliding along the opening 7 in the hinged door 4 and once again held in place by the teeth 23 once it reaches the bottom of the hinged door 4.

The second method for dispensing needles is shown in FIGS. 7 through 11. FIG. 7 shows the medication delivery pen device 18 staying attached to the pen cap 9. The entire assembly of the replacement pen cap disposal container and unused pen needle storage 32 with the medication delivery pen 18 is then inverted. FIG. 8 shows the user's thumb opening the hinged door 4 from point where the lid snaps on 25 to the walls 22 of the containment area 3. This is facilitated due to the living hinge 10 and the tabs 5, 6. The unused needles 1 are loaded into the unused needle storage area 3 so that their foil covered side 36 is flush with the rear wall 21 to the containment area 3 and the non-foil side 38 sticks through the opening 7 in the hinged door 4 as the door is closed by the thumb in FIG. 9. The door snaps shut at 25, and the needles are contained within the unused needle containment section 35. The entire replacement pen cap disposal container and unused pen needle storage 32 with the inserted medication delivery pen 18 is then flipped right side up once again. FIG. 10 then displays the user grabbing an unused pen needle 1 by its non-foil end 38, pulling it through the circular opening 24 to the triangular opening 7, and pulling the foil end 36 through the teeth 23 as they flex slightly. FIG. 11 then displays the remaining unused needles 1 falling into place in the unused needle containment area 3 after one unused pen needle 1 has been removed. The remaining unused pen needles 1 slide along the opening 7, with the bottom unused needle resting in the circular opening 24 with teeth 23, waiting to be pulled out dispensed again when needed.

FIGS. 12 through 14 display the disposal method for used medication delivery pen needle sharps 20. FIG. 12 shows a hand holding the sharps containment section 34 with the thumb using the tabs 12 located on either side of the lid 11 to open the hinged lid, allowing the used pen needle 20 to be placed inside (FIG. 13) the pre-containment area 27 with the non-foil side 38 placed into the angled lid assembly 33 closest to the living hinge 14 of the angled lid so that the used needle 20 is at a downward angle with the uncovered foil side 39 closest to the pen cap section 9. The angled lid assembly 33 allows for the flexible plastic teeth 13 to be longer than the used pen needle 20, even though the sharps disposal area 15 is only just slightly wider than the length of the used pen needle 20, and only slightly larger in depth than the diameter of the foil side of the used pen needle 39. It also allows for the thumb of the user to be protected from sharps due to both the lid 11 and the living hinge 14 blocking any needle from protruding. FIG. 13 then shows the used pen needle on top of the flexible plastic teeth 13, below the lid 11, in the pre-containment area 27, ready for the groove 29 on the lid 11 in which the user's thumb sits in to push the used pen needle 20 through the flexible plastic teeth 13, and into the sharps disposal area 15 non-foil end first 38. FIG. 13 shows the thumb executing this closing motion to the lid 11, pushing the used pen needle 20 into the sharps disposal area 15, and in FIG. 14 the used pen needle 20 falls preferentially horizontally into the sharps disposal area 15, much as it once sat in the unused needle containment section 35.

Figure 15:
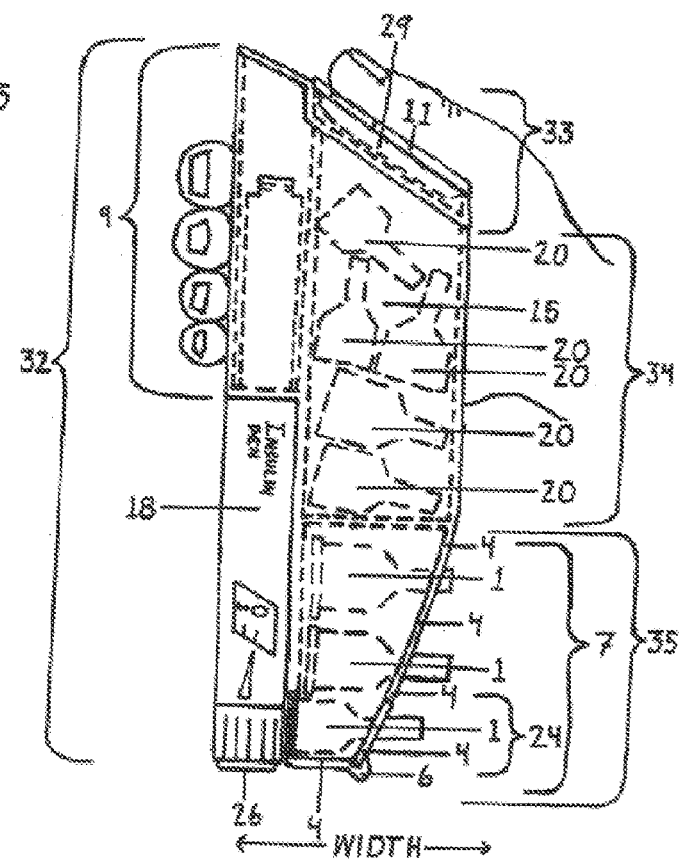
FIG. 15 is a side view of the base device with the medication delivery pen inserted showing a full base device with both used and unused needles, along with illustrating that two horizontal pen needles taking up the same space as two vertical needles.

FIG. 15 displays the full disposal container and unused pen needle storage 32 with the user's fingers ergonomically wrapping around the pen cap section 9, and the thumb resting in the groove 29 on the lid 11 of angled lid assembly 33. The sharps containment section is shown full at 34 with used needles 20 stacked both two horizontally 40 and two vertically 141. This is meant to display that due to the length of used pen needles 20 being twice their diameter, the amount of space it takes to stack two horizontally 40 is the same space it takes to stack two vertically 141 within the containment area. FIG. 15 also shows the unused needle containment section 35 full of unused needles 1 and the tabs 6 on the hinged door 4 forming a tripod with the bottom of the medication delivery pen 18. Note that the base device (disposal container and unused pen needle storage replacement cap) 32 adds surface area to the device as it sits in the user's pocket, decreasing the chance that the whole base device 32 would slip out of one's pocket, but minimizing the amount of space the medication delivery pen 18 sticks out of the pocket when carried due to the device having relatively the same depth as the pen is in diameter.

Figure 16:
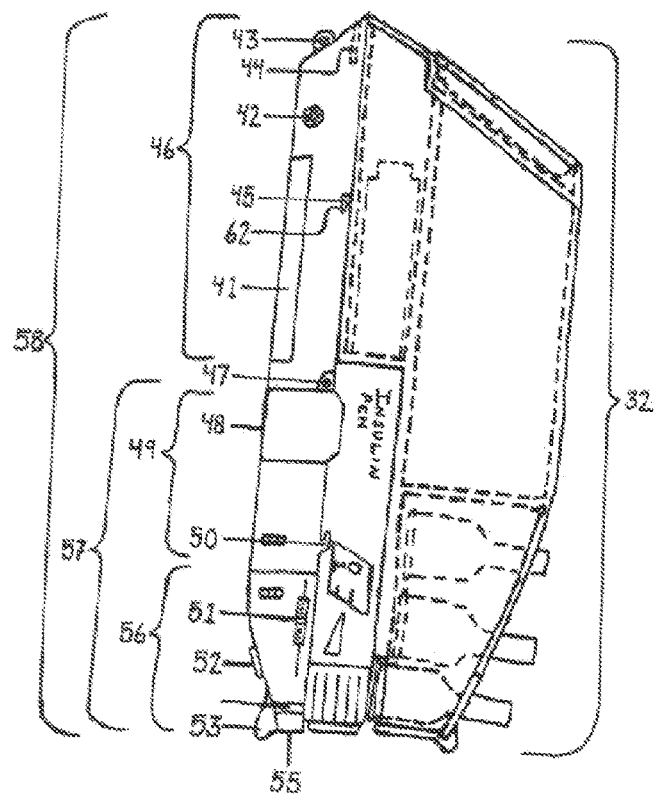
FIG. 16 shows a side view of the base device with the folding glucose monitor attachment.
Figure 17:
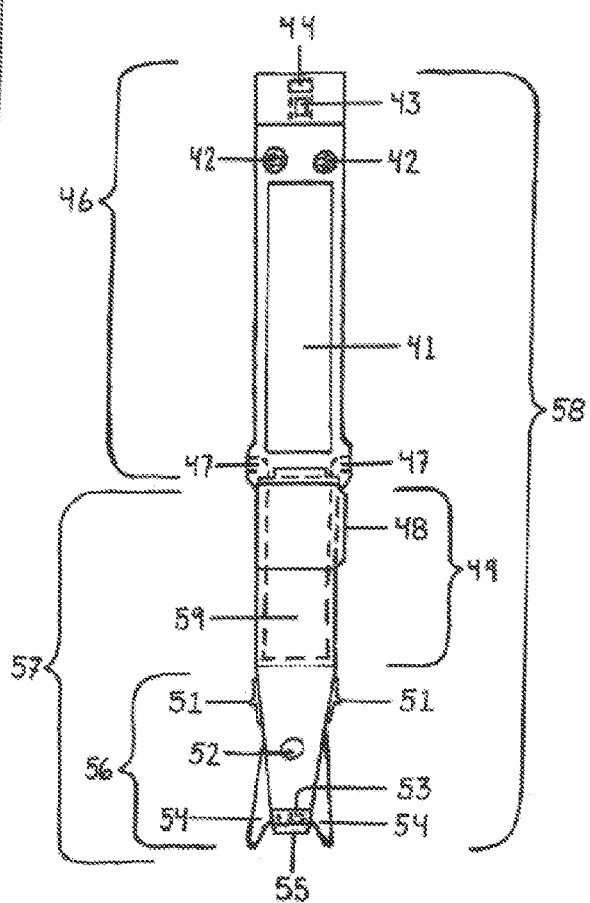
FIG. 17 shows a rear view of the base device with the folding glucose monitor attachment.

FIGS. 16 and 17 show the folding glucose monitor 58 that attaches to the disposal container and unused pen needle storage replacement cap's attachment point 45 with the glucose monitor's attachment point 62. The glucose monitor 46 that makes up the upper half of the folding glucose monitor 58 features a key chain hole 43, the glucose monitor's attachment point 62, buttons 42 to scroll on the glucose monitor 46, an insertion point for glucose testing strips 44, and a screen to view blood sugar testing results 41. The folding glucose monitor 58 folds on its hinge 47 that can be locked straight or folded. The lower half 57 of the folding glucose monitor 58 features a glucose testing strip holding container 49 with a door 48 that opens and covers the top of the container when the attachment is folded. The lancing device 56 that is the lower portion of the lower half 57 is made up of tabs 51 to pull back in order load the lancet so it can be fired through a hole 55 at the user's finger when the button 52 is pressed. It also features legs 54 to stand the device on, and a telescoping end 53 to adjust the depth that the lancet pierces the skin.

Figure 19:
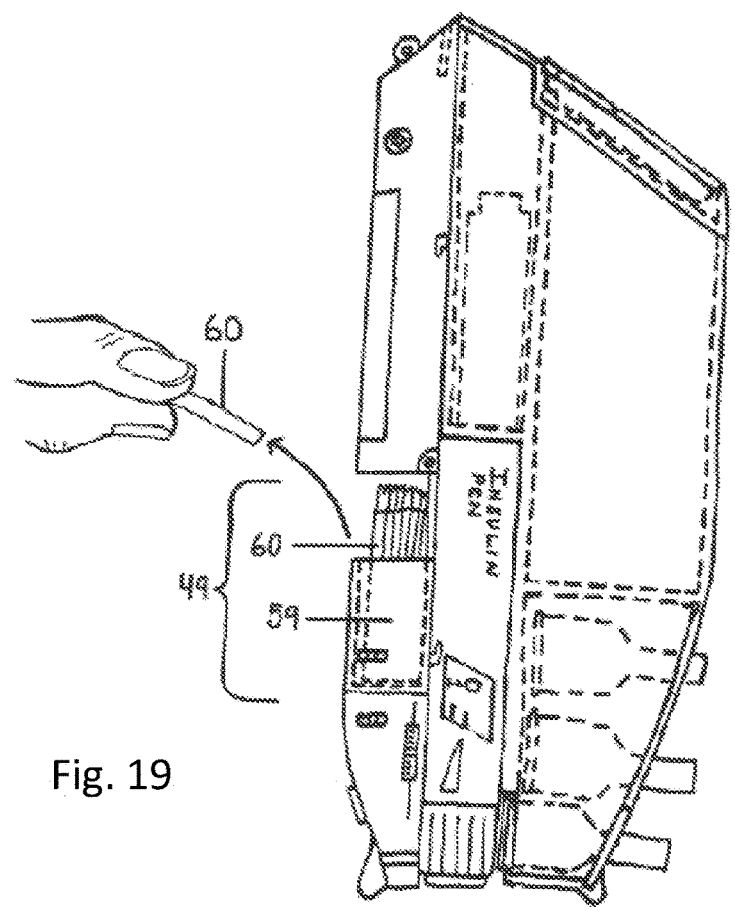
FIG. 19 shows a side view of the base device with the folding glucose monitor attached and the door to the glucose testing strip holder being opened, and test strip being pulled out.
Figure 18:
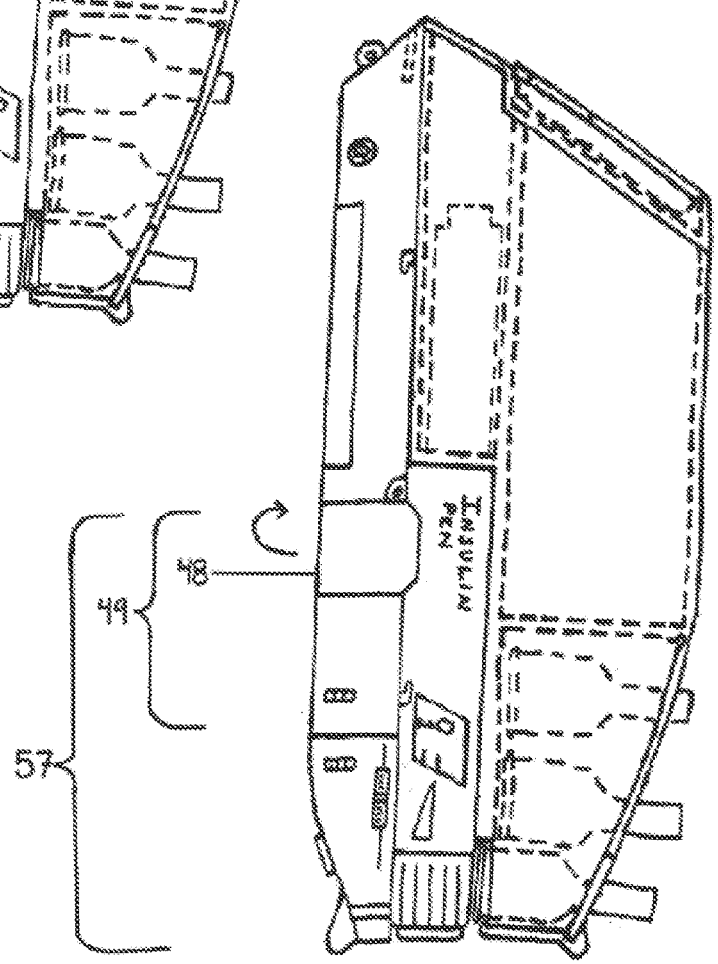
FIG. 18 shows a side view of the base device with the folding glucose monitor attached and the door to the glucose testing strip holder being opened.
Figure 20:
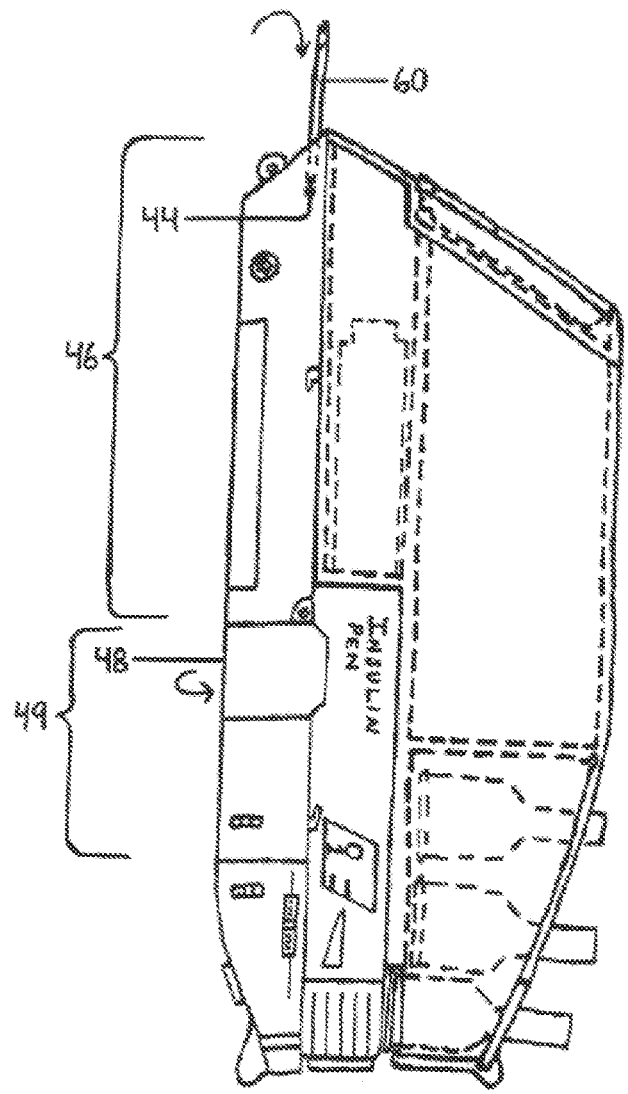
FIG. 20 shows a side view of the base device with the folding glucose monitor attached, the glucose testing strip being put into the glucose monitor, and the door to the glucose testing strip holder being closed.
Figure 21:
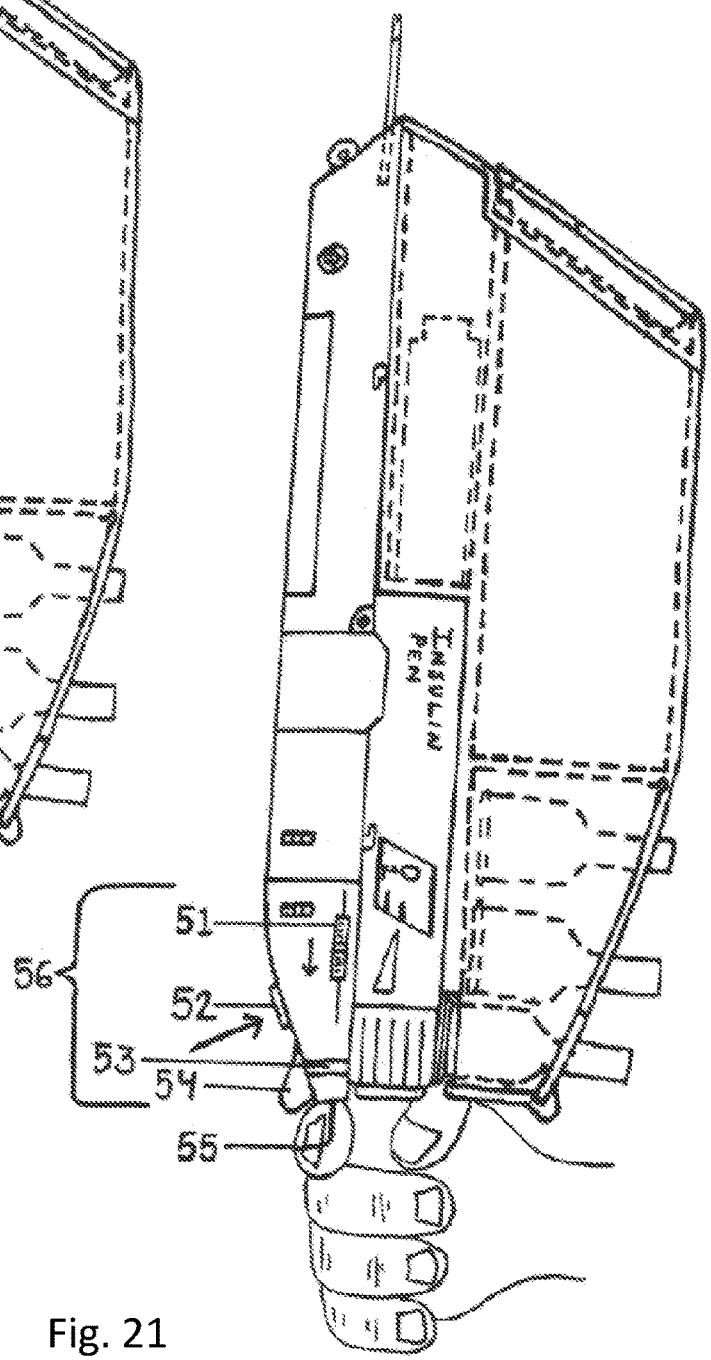
FIG. 21 shows a side view of the base device with the folding glucose monitor attached, a glucose test strip in the glucose monitor, and the lancing device pricking the user's finger to draw blood.
Figures 22, 23:
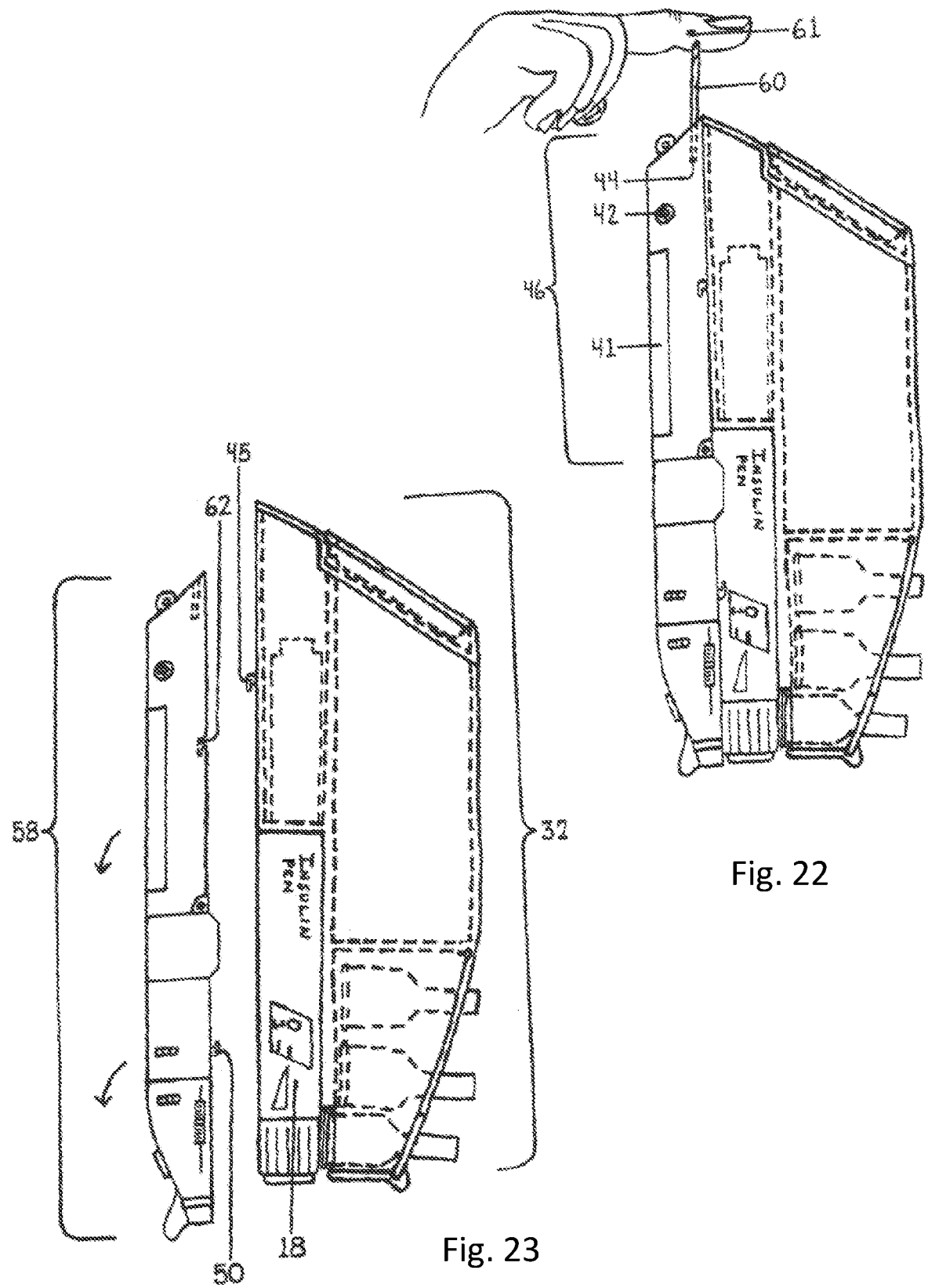
FIG. 22 shows a side view of the base device with the folding glucose monitor attached as the user puts a sample of their blood to the test strip in the folding glucose monitor in order to obtain the blood glucose of the user.
FIG. 23 shows a side view of the base device with the folding glucose monitor attachment being removed from the base device to be used separately.

FIGS. 18-22 show the folding glucose monitor 58 being used while attached to the disposal container and unused needle storage replacement cap 32. The glucose monitor's attachment point 62 attaches to the disposal container and unused needle storage replacement cap's attachment point 45. The door 48 to the glucose testing strip holding container 49 is shown being opened in FIG. 18. FIG. 19 shows a glucose test strip 60 being pulled from the bay 59 of the glucose testing strip holding container 49. FIG. 20 shows the glucose test strip 60 being inserted into the glucose monitor 46 through the test strip insertion point 44 at the top of the glucose monitor 46. The door 48 to the glucose testing strip holding container 49 is also shown being shut in FIG. 20. FIG. 21 shows the lancing device 56 being loaded and readied via tabs 51. The button 52 on the lancing device 56 is then shown being pressed thus firing the lancet at the user's finger through a hole 55. In order to adjust depth, the user can use the telescoping end 53 to the lancing device 56. The legs 54 on the folding glucose monitor 58 also serve to hold the user's finger in place as the lancing device 56 pricks their finger. FIG. 22 shows the user bringing the sample of blood 61 on their finger to the glucose test strip 60. The blood is drawn into the glucose test strip 60 and the glucose monitor 46 then reads the results through electrical connections to the glucose test strip 60 in the test strip insertion point 44 that the glucose test strip 60 is inserted into. The glucose monitor 46 then displays the results on the screen 41. The user can then scroll through the results using the buttons 42 on the device. It is important to note that the folding glucose monitor device 58 can be used in this same way when it left locked and straight and is detached from the disposal container and unused needle storage device 32.

Figure 24:
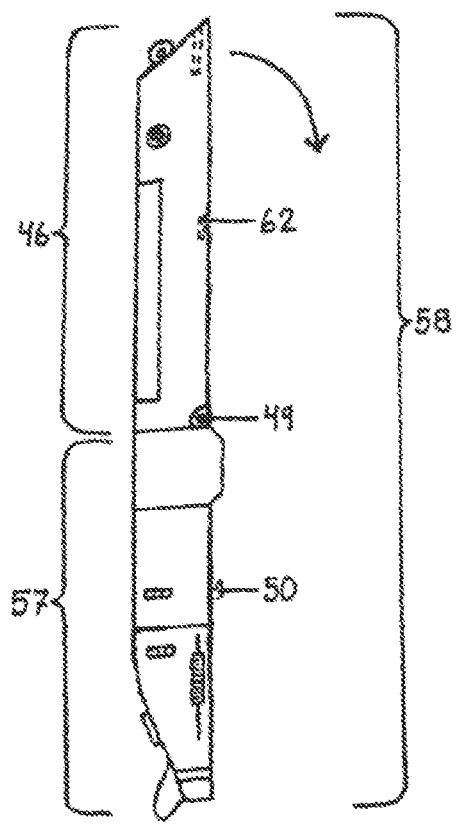
FIG. 24 shows a side view of the folding glucose monitor attachment as it is folded.

FIGS. 23-27 show the folding glucose monitor 58 being removed as an attachment, folded, and used separately. FIG. 23 shows the glucose monitor's attachment point 62 being detached from the disposal container and unused pen needle storage replacement cap's attachment point 45 as the folding glucose monitor 58 is pulled off the disposal container and unused needle storage device 32. FIG. 24 shows the folding glucose monitor 58 being folded at the hinge 47 so that the top half (the glucose monitor) 46 folds to match up with the bottom half 57. The folding glucose monitor 58 will fold so bottom half attachment point 50 would match up with the glucose monitor attachment point 62 and snap in. FIGS. 25A and 25B then show getting a test strip 60 out of the folded folding glucose monitor 58. FIG. 25A shows the door 48 to the glucose testing strip holding container 49 being opened.

Figure 25A:
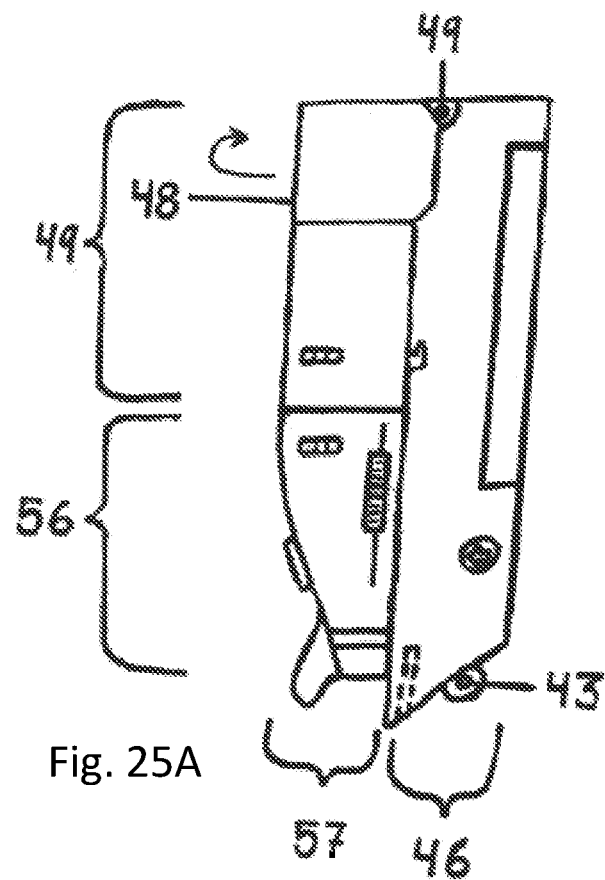
FIG. 25A shows a side view of the folded folding glucose monitor as the door to the glucose testing strip holder is being opened.
Figure 25B:
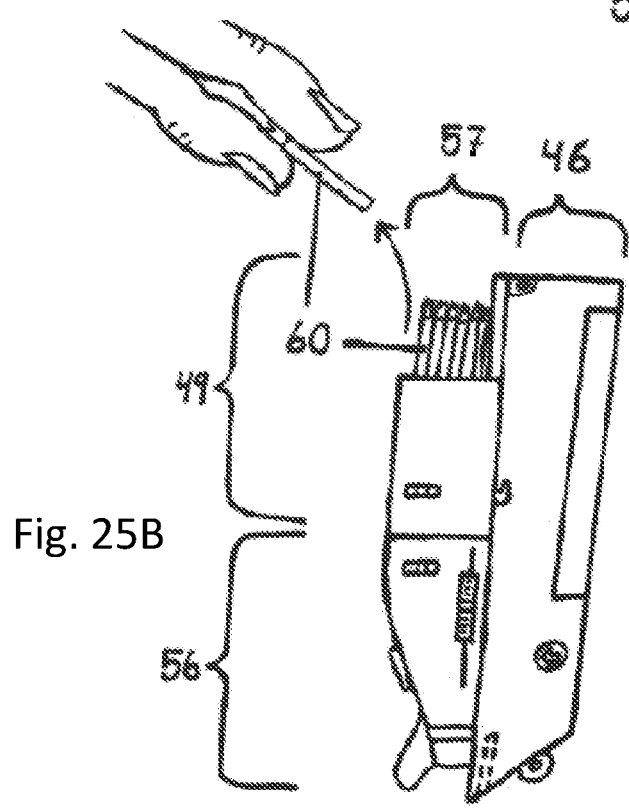
FIG. 25B shows a side view of the folded folding glucose monitor as the user pulls a glucose test strip from the glucose testing strip holder.
Figures 26A, 26B, 27:
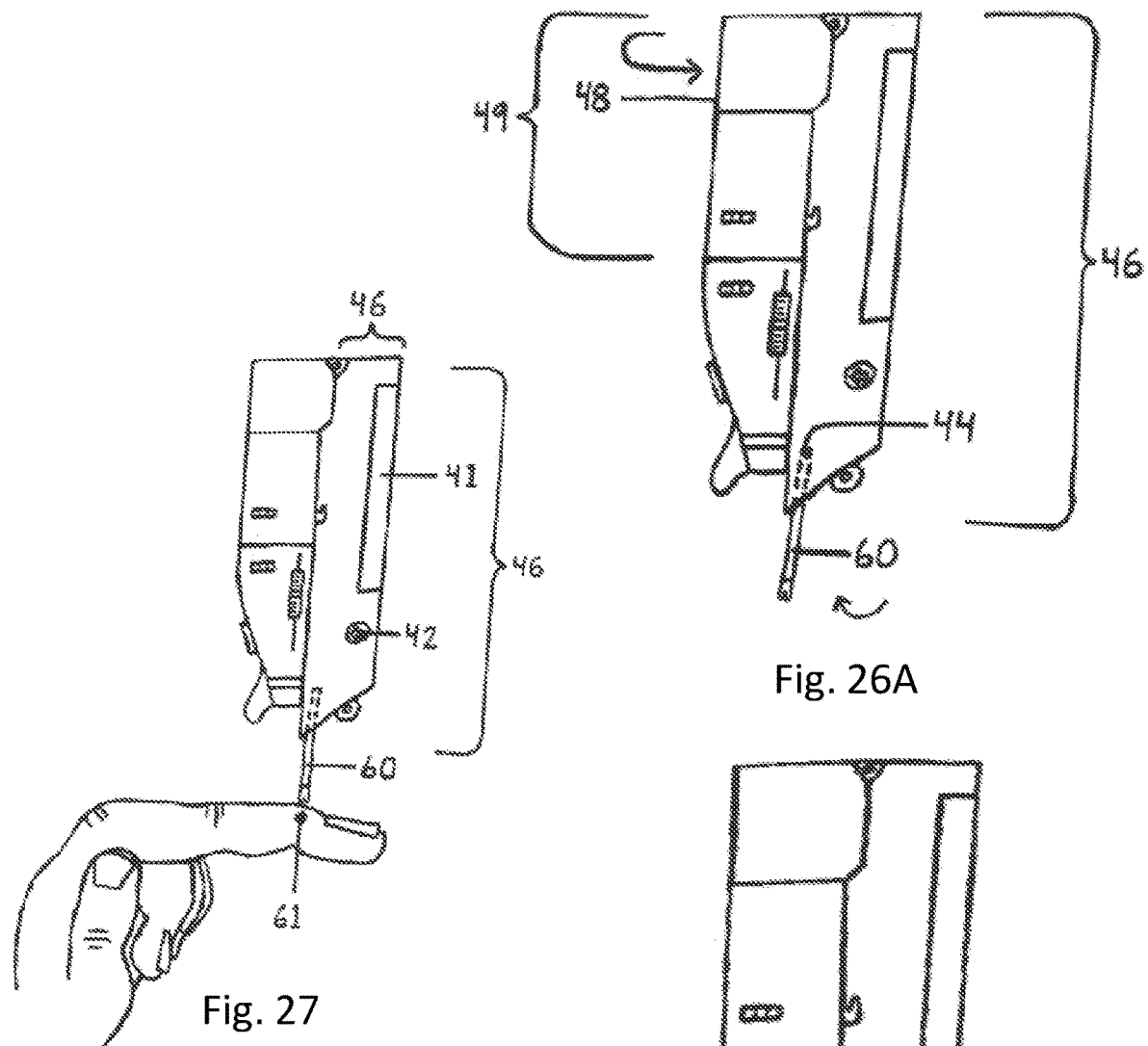
FIG. 26A shows a side view of the folded folding glucose monitor as the door to the glucose testing strip holder is closed and the glucose test strip is inserted into the monitor.
FIG. 26B shows a side view of the folded folding glucose monitor with a glucose test strip in the glucose monitor as the lancing device pricks the user's finger in order to draw blood.
FIG. 27 shows a side view of the folded folding glucose monitor as the user puts a sample of blood up to the testing strip in order to obtain a blood glucose.

The door 48 covers the roof to the glucose testing strip holding container 49, so when it is opened the testing strips 60 are left completely exposed. This is shown in FIG. 25B as a user pulls a testing strip 60 out of the bay 59 of the glucose testing strip holding container 49. In FIG. 26A the glucose test strip 60 is inserted into the glucose monitor 46 via the test strip insertion point 44 as the door 48 to the glucose testing strip holding container 49 is shut. FIG. 26B shows the user loading the lancing device 56 by pulling back the tabs 51 and pricking his finger by pressing the button 52 to release the lancet. The glucose monitor 46 and the legs 54 hold the users finger in place. The user can adjust the depth of the prick with the telescoping end 53. FIG. 27 shows the user bringing his blood sample 61 to the glucose test strip 60 that is in the glucose monitor 46. The glucose monitor 46 reads the sample and displays the results on the screen 41 which the user can scroll through with the buttons 42.

This folding and locking mechanism is a unique characteristic of the folding glucose monitor 58 and the invention as a whole, since currently no other glucose monitors fold in such a way. As well, the device, once folded, would be flat and so much easier to carry and hold than existing glucose monitor testing systems. Another unique characteristic is that it has a key chain hole and so it can be used as a key fob, increasing the chances that it will be carried, and pairing the device with the user's keys to reduce the number of devices the user needs to carry. This means keys can also be attached to the overall invention when the glucose monitor is attached.

Figure 28:
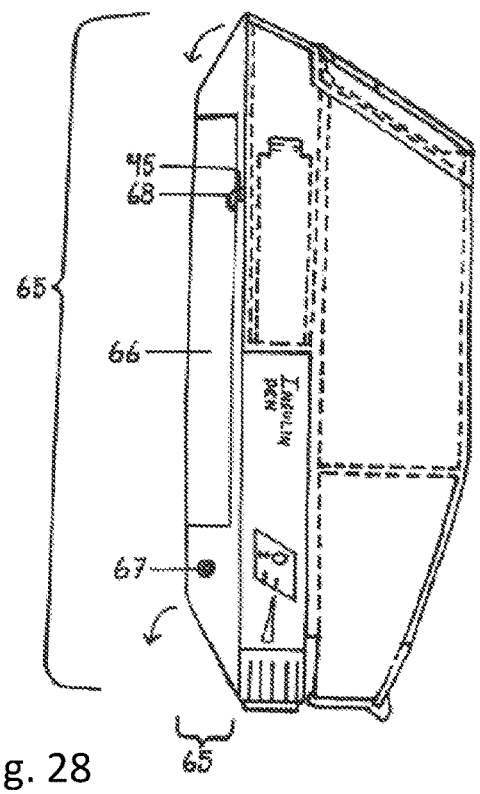
FIG. 28 shows a side view of the base device with the constant glucose monitor attachment.
Figure 29:
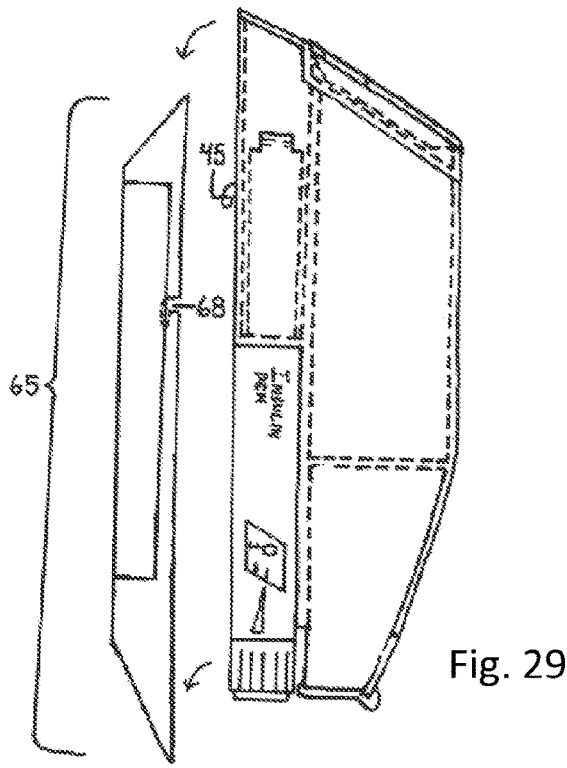
FIG. 29 shows a side view of the base device with the constant glucose monitor attachment being detached from the device for separate use.

FIGS. 28 and 29 show a constant glucose monitor 65 being detached from the disposal container and unused needle holder replacement cap 32. FIG. 28 shows the constant glucose monitor 65 being taken off by its attachment point 68 off of the disposal container/unused pen needle storage replacement cap's attachment point 45. The constant glucose monitor 65 features a screen 66 to display the information it receives wirelessly from a probe and buttons 67 to navigate the results. FIG. 29 shows the constant glucose monitor 65 taken off the disposal container/unused needle storage replacement cap 32 for use on its own or to be paired with the glucose tablets/candy attachment 73. This offers the user the most flexibility in its use and with that have the greatest convenience to the user.

Figure 30:
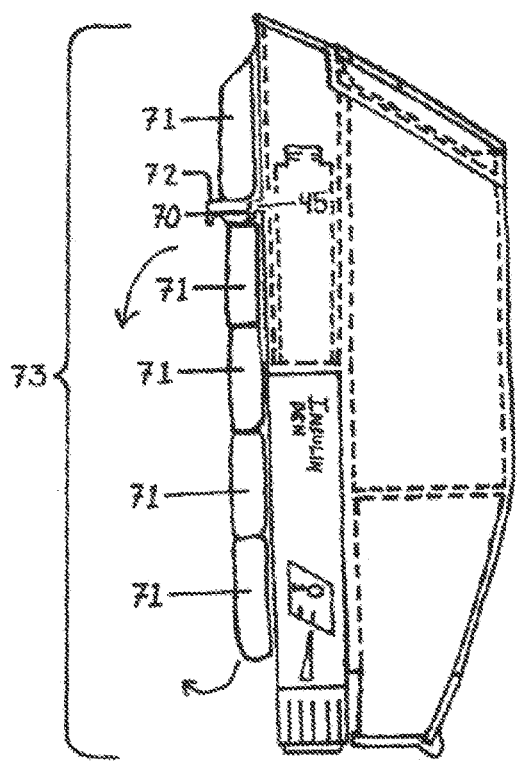
FIG. 30 shows a side view of the base device with the glucose tablet/candy attachment attached to the device.
Figure 31:
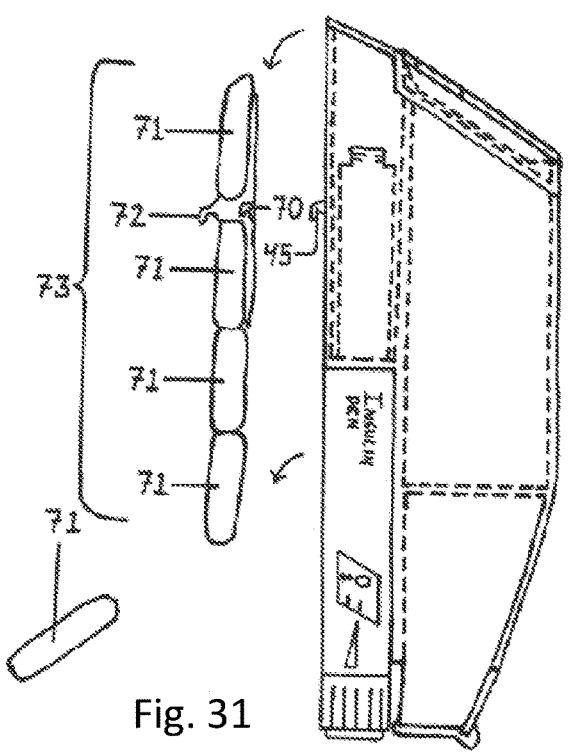
FIG. 31 shows a side view of the base device with the glucose tablet/candy attachment being detached, and a glucose tablet/candy being broken off for ingestion by the user.

FIGS. 30 and 31 shows the glucose tablets/candy attachment 73 being taken off and a glucose tablet/candy 71 being broken off to be ingested. FIG. 30 shows the glucose tablet/candy attachment 73 attached via its primary attachment point 70 to the replacement cap disposal container and unused pen needle storage replacement cap's attachment point 45. It is imperative to note that glucose tablet/candy attachment 73 also features a secondary attachment point 72 so the folding glucose monitor 58 or the constant glucose monitor 65 can be attached to the glucose tablets/candy attachment 73 by each of their own attachment points (62 and 68, respectively). This means that the glucose tablets can be carried alone, with one of the glucose monitors (58 or 65), with just the disposal container/unused needle holder disposable cap 32, or with all three devices at once. This gives the diabetic the most options and control over all three essential pieces to diabetic life. FIG. 31 shows the glucose tablets/candy attachment 73 being taken off the disposal container/unused needle holder's attachment point 45. A glucose tablet/candy 71 is broken off to raise a diabetic's blood sugar. Glucose/carbohydrates are the most critical part of diabetic's life since they pose the greatest immediate risk to their survival. Without something to raise blood glucose, a diabetic can go into shock or seizures within minutes. This is why the glucose tablets/candy attachment 73 serves to be the piece that has the most diverse carry options: so there is never a reason to leave it behind. This is why it features both the primary attachment point 70 and the secondary attachment point 72. The glucose/candy 71 will also be flat and compact so that it can easily fit between the two devices and take up as little room as possible, increasing the chances it will be carried.

In summary, the invention contemplates a disposable cap that replaces a cap to a medication delivery pen with either or both a sharps container attached to the side, and a gravity fed pen needle dispenser below the sharps container. This allows the patient to easily carry a medication delivery pen, its needles, and have a method to store contaminated sharps. Attached to this base device are supplementary devices that can be added or removed at the discretion of the user. These supplementary devices could also be attached to their own replacement pen cap for the medication delivery pen to be used individually with the medication delivery pen. They can also be stacked together or removed at the user's discretion. These attachments are a folding glucose monitor complete with a lancing device and a glucose testing strip holder, a constant glucose monitor, and glucose tablets/candy. All devices needed to check a diabetic's glucose, correct the blood glucose (with either ingestion of carbohydrates/glucose or an injection of insulin via the medication delivery pen), and dispose of all materials in the process is in one device. It also gives the user the most options and flexibility to fit any one or all of the devices into their lives as they please.

The sharps containment section includes an angled lid assembly that serves a number of purposes. First, the lid assembly's angled nature is ergonomic and natural in the way it fits in the user's hand. The angle of the lid assembly also causes the used pen needles to be pushed through non-foil side first so that they preferentially stack horizontally within the containment area, which leads to more efficient storage as a result. The angle of the lid assembly serves to increase the length of the area of flexible teeth so that used medication delivery pen needles pass through more easily.

The sharps container has a groove in the lid that both more completely pushes material out of the pre-containment area and into the containment area, but also prevents the user's thumb from slipping off the lid assembly. Finally, the lid and hinge run along the length of the user's thumb as to provide the most amount of protection to the user's thumb.

The sharps containment area, which is slightly wider as a medication delivery pen needle is long and in depth is slightly larger than the diameter of a medication delivery pen needle. This design allows for pen needles to stack in the most efficient way, forcing the first two (or all) medication delivery pen needles to fall horizontally or vertically, both taking up the same amount of space within the containment area so as to maximize storage potential. Horizontal stacking is preferable because it minimizes the chances of other needles being caught on each other and the lid assembly helps in ensuring this occurs, but is not perfect in its function at doing so.

The gravity fed pen needle dispenser is attached to the medication delivery pen via a replacement cap that has a loading and dispensing method that comprises a square opening slightly larger than the diameter of unused medication delivery pen needles that the medication delivery pen needles are fed into when the medication delivery pen is removed. When the medication delivery pen is replaced by being inserted into the cap the pen needles cannot fall out.

Once the medication delivery pen is removed once again, the unused pen needle falls out of the opening for use by the patient. The remaining needles fall into place ready to be dispensed due to gravity.

Another method of dispensing uses a loading method wherein the assembly is inverted, a hinged door is opened on the side opposite the square opening, the pen needles are placed horizontally within it, and the hinged door is closed with the pen needles sticking through that opening. The hinged door has a rounded triangular opening with teeth and the very lowest part being just bigger than the largest diameter of the unused pen needle due to the teeth protruding from the opening. This holds in the medication delivery pen needles until the user wishes, and when the user wishes the unused medication delivery pen needle could be pulled through this opening thanks to the flexing of the teeth in the opening. Remaining unused needles fall into this bottom part of the triangular opening due to gravity and are ready to be dispensed and used.

The folding glucose monitor attachment is designed with features to make it as compact and user friendly as possible. The glucose testing strip holder is in the center so it can be easily accessed when straight or folded and there is free access for the user's finger to the lancing device and glucose test strip when it is inserted into the monitor. A second feature is that the monitor is the same depth width and length as the lower half that comprises the lancing device and test strip holder. This makes the device able to be folded in half so that it is the same depth and flat, as the two halves match together. The folding mechanism is then also an important feature of this device since it lets the user choose between a long, pen style glucose monitor or a flat wider glucose monitor when detached. The folding mechanism also makes use of the same attachment point that it uses to attach to the disposal container and unused needle storage device to attach to itself. The placement of the monitor, glucose test strips, and lancing device is then ideal for both when the device is straight and when it is folded, so their placement is an important feature.

A glucose monitor, whether the constant glucose monitor or folding glucose monitor, attached to the medication delivery pen via a replacement cap allows for less devices to be carried by the diabetic in a more efficient manner. This is an important distinction to be made between this invention and existing devices or ideas, and this is true for the glucose monitor, the glucose tablets, the unused pen needle storage, and the disposal container. The idea of attaching devices the diabetic needs to the medication delivery pen via a replacement pen cap is a new idea and the focus of this invention.

Finally, the ability of the glucose tablets/candy attachment to have a second identical attachment point onto which the glucose monitor of the user's choice can attach to is another important feature. This allows all devices to fit together in the most space friendly and easy to use fashion. It also allows the user to carry the glucose tablets/candy with either the glucose monitor or the disposal container and unused needle storage cap at the discretion of the user. This is important because above all a diabetic needs to always have some form of glucose/carbohydrate with them since hypoglycemia (low blood sugar) poses the greatest immediate threat to a diabetic's life.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A packet comprising:
a medication delivery pen;
a pen cap releasably attached to the medication delivery pen, the pen cap integrally connected to an elongated body extending alongside the medication delivery pen and defining a storage chamber at one end and a disposal chamber at an opposite end;
the elongated body including a wall for isolating the storage chamber from the disposal chamber;
the storage chamber adapted to store a plurality of unused needles and having a dispensing opening for individually dispensing an unused needle; and
the disposal chamber adapted to contain a plurality of used needles and provided with a disposal opening for individually receiving a used needle into the disposal chamber, the disposal chamber including a flexible member extending at least partially across the disposal opening for retaining the used needle therein, and a lid for closing the disposal opening.

2. The packet according to claim 1 wherein the pen cap is configured to replace the pen cap normally supplied with the medication delivery pen and is integrally molded with the elongated body.

3. The packet according to claim 1 wherein the lid of the disposal chamber is angled relative to the elongated body.

4. The packet according to claim 1 wherein the lid and the disposal chamber define a pre-containment area for temporarily holding the used needle, and wherein the lid is operable to push the used needle into the disposal chamber when the lid is moved from an open position to a closed position.

5. The packet according to claim 1 wherein the dispensing opening is adapted to be blocked by the medication delivery pen when the medication delivery pen is inserted into and held by the pen cap.

6. The packet according to claim 5 wherein the unused needle is gravity fed into a dispensing position and held in a horizontal fashion.

7. The packet according to claim 1 wherein the wherein the dispensing opening is provided with a restriction which retains the unused needle until a pulling force is exerted on the unused needle by a user.

8. The packet according to claim 1 and further including a glucose monitor system as an attachment that includes a glucose monitor, a testing strip holder, and a lancing device.

9. The packet according to claim 8 wherein the attachment is foldable.

10. The packet according to claim 9 wherein the attachment folds flat due to a consistent depth of the attachment.

11. The packet according to claim 9 wherein a top portion of the attachment includes the glucose monitor and a bottom portion of the attachment includes the testing strip holder and the lancing device.

12. The packet according to claim 9 wherein the attachment folds so that the lancing device and a testing strip insertion point to the glucose monitor are adjacent to each other.

13. The packet according to claim 8 wherein the attachment forms a straight, pen-like device with the glucose monitor on one end, the testing strip holder in the middle, and the lancing device on the other end.

14. The packet according to claim 1 and further including a glucose monitor system including at least one of a glucose monitor, a testing strip holder, and a lancing device.

15. The packet according to claim 14 wherein the glucose monitor system is releasably attached to the pen cap.

* * * * *